US010832172B1

(12) United States Patent
Neumann

(10) Patent No.: US 10,832,172 B1
(45) Date of Patent: Nov. 10, 2020

(54) SYSTEMS AND METHODS FOR ARRANGING TRANSPORT OF ADAPTED NUTRIMENTAL ARTIFACTS WITH USER-DEFINED RESTRICTION REQUIREMENTS USING ARTIFICIAL INTELLIGENCE

(71) Applicant: KPN INNOVATIONS, LLC., Lakewood, CO (US)

(72) Inventor: Kenneth Neumann, Lakewood, CO (US)

(*) Notice: Subject to any disclaimer, the term of this patent is extended or adjusted under 35 U.S.C. 154(b) by 0 days.

(21) Appl. No.: 16/547,678

(22) Filed: Aug. 22, 2019

(51) Int. Cl.
*G06N 20/00* (2019.01)
*G16H 20/60* (2018.01)

(52) U.S. Cl.
CPC ............. *G06N 20/00* (2019.01); *G16H 20/60* (2018.01)

(58) Field of Classification Search
CPC ...................................................... G06N 20/00
See application file for complete search history.

(56) References Cited

U.S. PATENT DOCUMENTS

| | | | | |
|---|---|---|---|---|
| 6,490,573 | B1* | 12/2002 | Njemanze | G06N 3/04 |
| | | | | 706/19 |
| 8,560,334 | B2 | 3/2013 | Laehteenmaeki | |
| 10,127,361 | B2 | 11/2018 | Hyde et al. | |
| 2005/0080650 | A1 | 4/2005 | Noel | |
| 2007/0094090 | A1 | 4/2007 | Jenkins | |
| 2013/0304488 | A1 | 11/2013 | Girao et al. | |
| 2015/0079551 | A1* | 3/2015 | Egan | G09B 19/0092 |
| | | | | 434/127 |
| 2015/0363860 | A1 | 12/2015 | Lantrip et al. | |
| 2015/0371553 | A1 | 12/2015 | Vento | |
| 2016/0307128 | A1 | 10/2016 | Herman et al. | |
| 2018/0182479 | A1 | 6/2018 | Castellon et al. | |
| 2018/0189636 | A1 | 7/2018 | Chapela et al. | |

(Continued)

OTHER PUBLICATIONS

Burca, David, Manuel Schüller, and Johannes Zlabinger. "Case-based Reasoning and Machine Learning." May 2018. (Year: 2018).*

(Continued)

*Primary Examiner* — Eric Nilsson
(74) *Attorney, Agent, or Firm* — Caldwell Intellectual Property Law

(57) ABSTRACT

A system for arranging transport of adapted nutrimental artifacts with user-defined restriction requirements using artificial intelligence. The system includes at least a user-client device designed and configured to display at least an unrestricted nutrimental object, transmit at least a restricted nutrimental datum, transmit at least an adapted nutrimental request, and receive a selection of at least a sustenance provider and a selection of at least a physical performer. The system includes at least a server designed and configured to receive at least a restricted nutrimental datum. The system includes a nutrimental processing module operating on the at least a server designed and configured to generate at least a first filter set and transmit at least a first filter set. The system includes a nourishment provider module operating on the at least a server design and configured to generate at least a sustenance provider instruction set and at least a physical performer instruction set, and select the at least a sustenance provider and the at least a physical performer.

16 Claims, 14 Drawing Sheets

(56) References Cited

U.S. PATENT DOCUMENTS

2018/0190375 A1* 7/2018 Chapela ................. G09B 19/00
2018/0204274 A1 7/2018 Shimokawa et al.
2018/0240542 A1* 8/2018 Grimmer ............ G06F 16/9535
2019/0290172 A1* 9/2019 Hadad ................... G06N 20/00

OTHER PUBLICATIONS

Calegari, L. P., et al. "A conjoint analysis to consumer choice in Brazil: Defining device attributes for recognizing customized foods characteristics." Food research international;109 (2018): 1-13. (Year: 2018).*

Maldarelli, Calire; Popular Science, Oct. 25, 2016; A personalized nutrition company will use your DNA to tell you what to eat; https://www.popsci.com/personalized-nutrition-company-will-use-your-dna-to-tell-you-what-to-eat.

Polito, Lisa; Dec. 2, 2016; 3 companies expand the possibilities of personalized nutrition; https://www.newhope.com/products-and-trends/3-companies-expand-possibilities-personalized-nutrition.

Jones, Alexandra; Sep. 22, 2018; The Guardian; Blood, spit and swabs: can you trust home medical-testing kits?; https://www.theguardian.com/global/2018/sep/22/home-medical-testing-kits-blood-spit-swabs-trust-diy.

Habit Food Personalized; 2019; https://habit.com/how-it-works/.

Van Ommen, et al.; Nutrition Reviews vol. 75; Systems biology of personalized nutrition; https://watermark.silverchair.com/nux029.pdf?.

* cited by examiner

| Product Category: Desserts |
|---|
| Apple pie |
| Apple fritter |
| Banana pudding |
| Blueberry pie |
| Bread pudding |
| Carrot cake |
| Cherry pie |
| Chocolate brownies |
| Chocolate cake |
| Chocolate chip cookies |
| Cheesecake - plain |
| Cheesecase w/ strawberries |
| Chocolate fudge |
| Funnel Cake |
| Key lime pie |
| Lemon bar |
| Lemon custard |
| Lemon drops |
| Lemon meringue pie |
| Meringue |
| Mouse cake |
| Napoleon pastry |
| Peanutbutter cookies |
| Pudding - chocolate |
| Pudding - vanilla |
| Red velvet cake |

304

| Product Category: Desserts |
|---|
| Banana pudding |
| Blueberry pie |
| Bread pudding |
| Carrot cake |
| Cherry pie |
| Cheesecake - plain |
| Cheesecase w/ strawberries |
| Funnel Cake |
| Key lime pie |
| Lemon bar |
| Lemon custard |
| Lemon drops |
| Lemon meringue pie |
| Meringue |
| Peanutbutter cookies |
| Pudding - vanilla |

| Meals | Portion (g) | Nutritional Information | | | | | |
|---|---|---|---|---|---|---|---|
| | | Protein (g) | Carbohydrates (g) | Total Fat (g) | Cholesterol (mg) | Iron (mg) | Sodium (mg) |
| Roasted lamb leg; carrots; mashed potatoes | 75 | 19 | 5 | 12 | 70 | 1.5 | 50 |
| Roasted lamb leg; carrots; white bread role | 75 | 16 | 10 | 22 | 73 | 1.2 | 55 |
| Roasted chicken drumstick w/ skin; carrots; corn | 75 | 20 | 0 | 18 | 70 | 2 | 60 |
| Roasted chicken drumstick; carrots; corn | 75 | 19 | 0 | 9 | 40 | 2 | 40 |
| Fried, breaded chicken drumstick; carrots; corn | 75 | 16 | 0 | 10 | 68 | 1 | 68 |
| Fried, breaded chicken drumstick; roasted spinach | 75 | 19 | 0 | 5 | 70 | 1 | 71 |
| Roasted chicken thigh w/ skin; carrots; corn | 75 | 22 | 0 | 22 | 80 | 1 | 63 |
| Roasted chicken thigh w/ skin; carrots; wheat bread | 75 | 19 | 11 | 5 | 71 | 2 | 66 |
| Roasted duck thigh w/ skin; carrots; corn | 75 | 14 | 0 | 21 | 63 | 2 | 44 |
| Roasted duck thigh w/ skin; roasted spinach | 75 | 23 | 0 | 3 | N/A | 7.4 | 40 |

408

Preferences

| Price per meal | Distance from location | Supplemental provider type |
|---|---|---|
| $10-20 | Maximum of 20 miles | Home chef |

| Meals | Nutritional Information |||||||| Options ||
| --- | --- | --- | --- | --- | --- | --- | --- | --- | --- |
| | Portion (g) | Protein (g) | Carbohydrates (g) | Total Fat (g) | Cholesterol (mg) | Iron (mg) | Sodium (mg) | Gluten | Oil |
| Roasted lamb leg; carrots; mashed potatoes | 75 | 19 | 5 | 12 | 70 | 1.5 | 50 | N | Grapeseed |
| Roasted chicken drumstick w/ skin; carrots; corn | 75 | 20 | 0 | 18 | 70 | 2 | 60 | N | Olive |
| Roasted chicken drumstick; carrots; corn | 75 | 19 | 0 | 9 | 40 | 2 | 40 | N | Olive |
| Roasted chicken thigh w/ skin; carrots; corn | 75 | 22 | 0 | 22 | 80 | 1 | 63 | N | Olive |
| Roasted duck thigh w/ skin; carrots; corn | 75 | 14 | 0 | 21 | 63 | 2 | 44 | N | Olive |
| Roasted duck thigh w/ skin; roasted spinach | 75 | 23 | 0 | 3 | 60 | 7.4 | 40 | N | Olive |

508

Preferences

| Price per meal | Distance from location | Supplemental provider type | Meals per person |
| --- | --- | --- | --- |
| $10-20 | Maximum of 20 miles | Home chef | Triple the quantity of each meal to feed 3 people |

SYSTEMS AND METHODS FOR ARRANGING TRANSPORT OF ADAPTED NUTRIMENTAL ARTIFACTS WITH USER-DEFINED RESTRICTION REQUIREMENTS USING ARTIFICIAL INTELLIGENCE

FIELD OF THE INVENTION

The present invention generally relates to the field of artificial intelligence. In particular, the present invention is directed to systems and methods for arranging transport of adapted nutrimental artifacts with user-defined restriction requirements.

BACKGROUND

Customization of nutrimental items to meet the dietary requirements of a user via network communication remains limited. In particular, solutions are lacking which include user specific requests and restrictions.

SUMMARY OF THE DISCLOSURE

In one aspect, a system for arranging transport of adapted nutrimental artifacts with user-defined restriction requirements using artificial intelligence includes at least a user-client device containing at least an exhibition element and a processor and connected to at least a central network, the at least a user-client device designed and configured to display at least an unrestricted nutrimental object on the at least an exhibition element, transmit at least a restricted nutrimental datum, transmit at least an adapted nutrimental request, and receive a selection of at least a sustenance provider and a selection of at least a physical performer. The system includes at least a server, connected to the at least a central network, the at least a server designed and configured to receive the at least a restricted nutrimental datum. The system includes a nutrimental processing module operating on the at least a server, the nutrimental processing module designed and configured to generate at least a first filter set as a function of the at least a restricted nutrimental datum, transmit the at least a first filter set to the at least a user-client device. The system includes a nourishment provider module operating on the at least a server, the nourishment provider module designed and configured to receive the at least an adapted nutrimental request, receive at least a sustenance provider datum, and at least a physical performer datum, generate at least a sustenance provider instruction set and at least a physical performer instruction set as a function of the at least a sustenance provider datum and the at least a physical performer datum and the adapted nutrimental request, select the at least a sustenance provider and the at least a physical performer as a function of the at least a sustenance provider instruction set and the at least a physical performer instruction set, and transmit the selection of the at least a sustenance provider and the selection of the at least a physical performer to the at least a user-client device.

In another aspect, a method of generating restriction requirements with at least a user-client device for transport of adapted nutrimental artifacts using artificial intelligence includes displaying by at least a user-client device at least an unrestricted nutrimental object. The method includes receiving by the at least a user-client device at least an element of user data containing at least a restriction requirement datum. The method includes generating by the at least a user-client device at least a restricted nutrimental datum as a function of the at least a restriction requirement datum. The method includes receiving by the at least a user-client device at least a first filter set. The method includes transmitting by the at least a user-client device at least an adapted nutrimental request to at least a sustenance provider and to at least a physical performer. The method includes receiving by the at least a user-client device at least a selection datum containing at least a sustenance provider and at least a physical performer. The method includes displaying by the at least a user-client device at least a confirmation screen.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 3 is a block diagram illustrating an exemplary embodiment of a display of nutrimental objects on a user-client device;

FIG. 4 is a block diagram illustrating an exemplary embodiment of a display of nutrimental artifacts on a user-client device;

FIG. 5 is a block diagram illustrating an exemplary embodiment of a display of nutrimental artifacts with restrictions on a user-client device;

The drawings are not necessarily to scale and may be illustrated by phantom lines, diagrammatic representations and fragmentary views. In certain instances, details that are not necessary for an understanding of the embodiments or that render other details difficult to perceive may have been omitted.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for arranging transport of adapted nutrimental artifacts with user-defined restriction requirements using artificial intelligence. In an embodiment, a user enters preferences regarding nutrimental restrictions for transport of adapted nutrimental artifacts. Further, sustenance providers and physical performers selected for preparation and transport of such restricted nutrimental artifacts are subject to a selection function accounting for these multiple restrictions. Loss function analysis may balance factors; this may be done by reference to an iteratively generated expression of preferential allocations of such restrictions, for instance by using machine-learning processes to acquire accurate pictures of user preferences.

Figure 1:
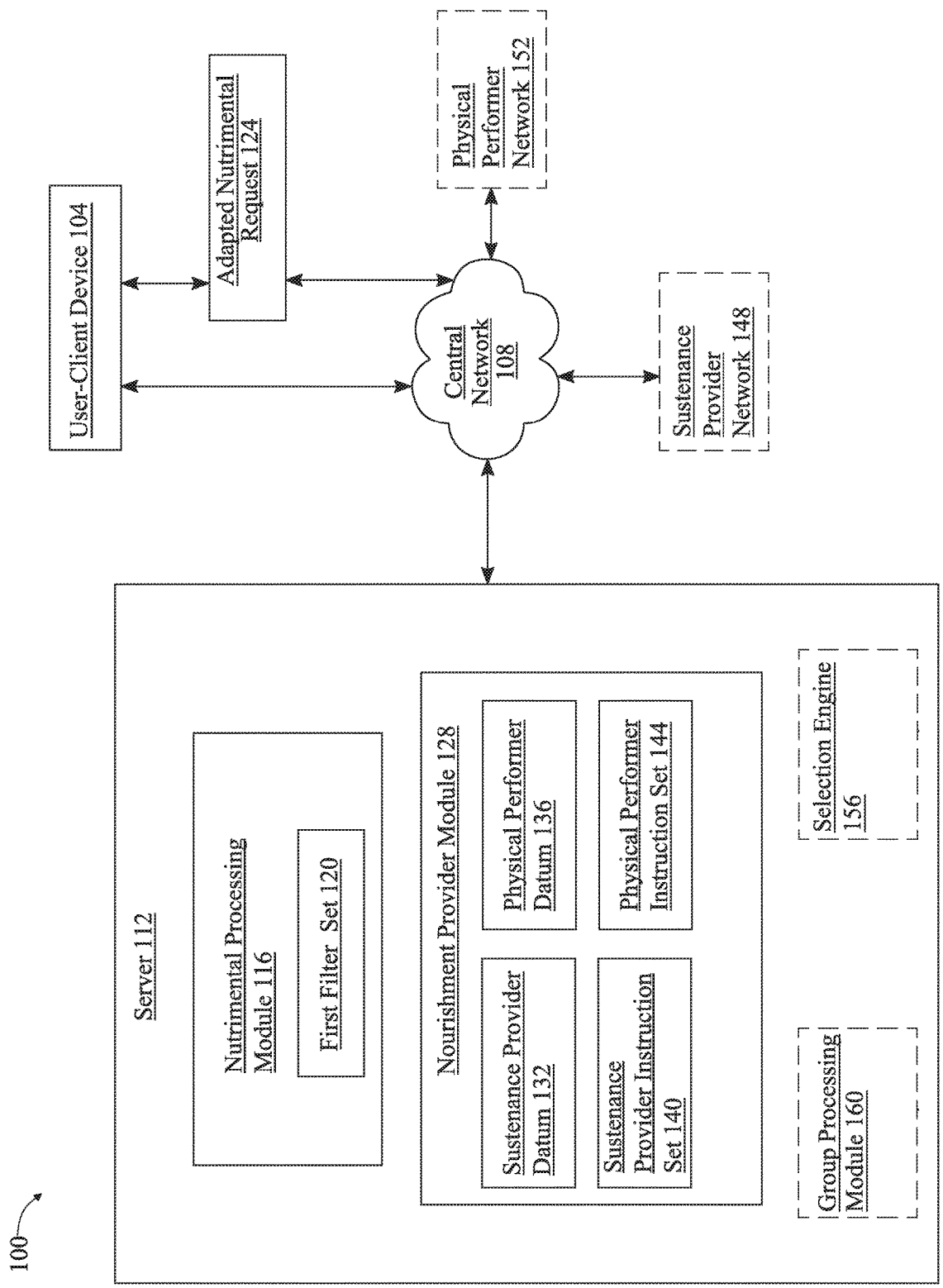
FIG. 1 is a block diagram illustrating an exemplary embodiment of a system for arranging transport of adapted nutrimental artifacts with user-defined restriction requirements.

Referring now to FIG. 1, an exemplary embodiment of a system 100 for arranging transport of adapted nutrimental artifacts with user-defined restriction requirements is illustrated. System 100 includes at least a user-client device 104, containing at least an exhibition element and a processor and connected to at least a central network. Exhibition element includes any hardware or software module. Exhibition element includes a graphical user interface (GUI). Graphical user interface, which may include without limitation a form or other graphical element having data entry fields, wherein one or more users, may enter information describing one or more user preferences and selections as described in more detail below. Fields in graphical user interface may provide, for instance in "drop-down" lists, where users may be able to select one or more entries to indicate their preference and/or selections. Fields may include free-form entry fields such as text-entry fields where a user may be able to type or otherwise enter text. User-client device 104 may include an additional computing device, such as a mobile device, laptop, desktop computer and/or workstation operated by a user. At least a user-client device 104 is connected to at least a central network 108 and including an exhibition element and a processor. At least a user-client device 104 may be a mobile device operated by a user who may be seeking to place an order of nutrimental artifacts or adapted nutrimental artifacts.

With continued reference to FIG. 1, user-client device 104 contains at least a processor. A processor may also be referred to as a central processing unit (CPU), central processor, or main processor, and is the electronic circuitry within a computer that carries out the instructions of a computer program by performing the basic arithmetic, logic, controlling, and input/output (I/O) operations specified by the instructions. Traditionally, the term "CPU" refers to a processor, more specifically to its processing unit and control unit (CU), distinguishing these core elements of a computer from external components such as main memory and I/O circuitry. Principal components of a CPU include the arithmetic logic unit (ALU) that performs arithmetic and logic operations, processor registers that supply operands to the ALU and store the results of ALU operations and a control unit that orchestrates the fetching (from memory) and execution of instructions by directing the coordinated operations of the ALU, registers and other components.

Most modern CPUs are microprocessors, meaning they are contained on a single integrated circuit (IC) chip. An IC that contains a CPU may also contain memory, peripheral interfaces, and other components of a computer; such integrated devices are variously called microcontrollers or systems on a chip (SoC). Some computers employ a multi-core processor, which is a single chip containing two or more CPUs called "cores"; in that context, one can speak of such single chips as "sockets". Array processors or vector processors have multiple processors that operate in parallel, with no unit considered central. There also exists the concept of virtual CPUs which are an abstraction of dynamical aggregated computational resources.

With continued reference to FIG. 1, user-client device 104 is connected to at least a central network 108. At least a central network 108 may include any hardware or software component. At least a central network 108 may include any of the network components as described below within this disclosure. At least a central network 108 may allow for connection of devices within system 100. Devices may include for example, desktop computer, laptop, mainframe, server, console, firewall, bridge, repeater, network interface card, switch, hub, modem, router, smartphone, tablet, webcam and the like. At least a central network 108 may be configured with different network topology including for example, mesh topology, ring topology, star topology, tree topology, bus topology, and the like.

With continued reference to FIG. 1, system 100 includes at least a server 112. At least a server 112 is connected to the at least a central network 108. At least a server 112 may include any computing device as described herein, including without limitation a microcontroller, microprocessor, digital signal processor (DSP) and/or system on a chip (SoC) as described herein. At least a server 112 may be housed with, may be incorporated in, or may incorporate one or more sensors of at least a sensor. Computing device may include, be included in, and/or communicate with a mobile device such as a mobile telephone or smartphone. At least a server 112 may include a single computing device operating independently, or may include two or more computing device operating in concert, in parallel, sequentially or the like; two or more computing devices may be included together in a single computing device or in two or more computing devices. At least a server 112 may include one or more additional devices as described below in further detail via a network interface device. Network interface device may be utilized for connecting at least a server 112 to one or more of a variety of networks, and one or more devices. Examples of a network interface device include, but are not limited to, a network interface card (e.g., a mobile network interface card, a LAN card), a modem, and any combination thereof. Examples of a network, such as at least a central network 108, include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 112 may include but is not limited to, for example, at least a server 112 or cluster of computing devices in a first location and a second computing device or cluster of computing devices in a second location. At least a server 112 may include one or more computing devices dedicated to data storage, security, distribution of traffic for load balancing, and the like. At least a server 112 may distribute one or more computing tasks across a plurality of computing devices of computing device, which may operate in parallel, in series, redundantly, or in any other manner used for distribution of tasks or memory between computing devices. At least a server 112 may be implemented using a "shared nothing" architecture in which data is cached at the worker, in an embodiment, this may enable scalability of system 100 and/or computing device.

With continued reference to FIG. 1, at least a server 112 and/or one or more modules operating thereon may be designed and/or configured to perform any method, method step, or sequence of method steps in any embodiment described in this disclosure, in any order and with any degree of repetition. For instance, at least a server 112 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 112 and/or one or more modules operating thereon may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, at least a user-client device 104 is designed and configured to display an at least an unrestricted nutrimental object on an exhibition element, transmit at least a restricted nutrimental datum to the at least a central network 108, transmit at least an adapted nutrimental request to the at least a central network 108, and receive a selection of at least a sustenance provider and a selection of at least a physical performer. An "unrestricted nutrimental object" as used herein includes nutrimental artifacts which have no user-imposed restrictions, preferences, limitations, or the like which are displayed on a user-client device 104. "Nutrimental artifacts include vegetables, fruits, dairy products, grains, beans, legumes, meat, confections, and the like which are able to be combined and/or prepared by a culinary professional into at least an edible food item or meal, or an ingestible beverage. Nutrimental artifacts may further include the type of preparation such as cooking, dressing, marinating, and/or any other food or beverage preparation process. Nutrimental artifacts may further include flavoring, seasoning, sauces, and/or any comestible product that may be used as an ingredient in a food or beverage. "Adapted nutrimental artifacts" as used herein may include nutrimental artifacts which have user-imposed restrictions, preferences, limitations, or the like, and is used synonymously with "restricted nutrimental artifacts". "At least a first restricted nutrimental object" and "at least a second restricted nutrimental object" may be considered adapted nutrimental artifacts which are displayed on a user-client device 104. "Restricted nutrimental datum", includes personal information uploaded by a user to a user-client device 104 which may be transmitted to at least a central network 108 to modify display of nutrimental artifacts on user-client device 104. "Adapted nutrimental request" is a data structure or any other compilation of data which may include at least an element of user data and at least a nutrimental artifact, the at least an element of user data describing the user, user needs, and/or user preference. "Sustenance provider," as described herein, is an entity that performs the preparation of a nutrimental artifacts. "Physical performer," as used herein, includes any transportation channel that executes the transport of nutrimental artifacts prepared by a sustenance provider. A more detailed description of terms mentioned herein can be found below in further reference to FIG. 1 and to FIG. 2.

With continued reference to FIG. 1, wherein generating at least a restricted nutrimental datum by a user client-device 104 may further involve receiving at least a user input variable containing at least a user nutrimental preference input, generating a loss function as a function of the at least a user input variable, and minimizing the loss function. In an embodiment, generation the at least a restricted nutrimental datum may be performed by a plurality of non-limiting mathematical algorithms, loss functions, and/or machine learning calculations. A "user input variable," as used herein, may relate to at least a restriction requirement datum uploaded to the user-client device 104, for example nutrimental preferences, sustenance provider preferences, physical performer preferences, or preferences to focus on any specific aspect of personal information uploaded, such as for example a medical test result, medical condition, allergies, fitness goal, or the like. "User nutrimental preference input," as used herein, may be a user input variable which contains a user's likes, dislikes, preferences, or exclusions to specific individual or groups of nutrimental artifacts. In an embodiment, user-device 104 may compare one or more user nutrimental preference inputs to one another with a mathematical expression representing an optimal combination of user entered variables. Mathematical expression may include a linear combination of variables, weighted by coefficients representing relative importance of each user nutrimental preference input in generating an optimal at least a restricted nutrimental datum. For instance, a user nutrimental preference input such as a dislike for broccoli may be multiplied by a first coefficient representing the importance of the dislike for broccoli, a second user nutrimental preference input such as preference for vegetarian meals may be multiplied by a second coefficient representing the importance of vegetarian meals, a degree of variance from any other user variable input may be represented as another parameter, which may be multiplied by an additional coefficient representing an importance of that variable; persons skilled in the art, upon reviewing the entirety of this disclosure, will be aware of different user input variables that may be weighted by various coefficients. Use of a linear combination is provided only as an illustrative example; other mathematical expressions may alternatively or additionally be used, including without limitation higher-order polynomial expressions or the like.

With continued reference to FIG. 1, wherein transmitting the at least a restricted nutrimental datum by the user-client device may further include displaying a discretionary restriction requirement field and uploading an at least a restriction requirement datum to the discretionary restriction requirement field.

With continued reference to FIG. 1, at least a server 112 is designed and configured to receive the at least a restricted nutrimental datum. "Restricted nutrimental datum", as used herein, includes personal information uploaded by a user to a user-client device 104 which may be transmitted to at least a central network 108 and used for generation of at least a first filter set which may restrict display of nutrimental artifacts on the user device 104 which coincide with selection of specific filters in the at least a first filter set. As a non-limiting example, a user may upload personal information showing an allergy to peanuts and a high blood cholesterol level to the user-client device 104, wherein at least a first filter set may be generated corresponding to this information allowing the user to filter out display of nutrimental artifacts which contain peanuts and/or are high in cholesterol. Further details about the contents of this paragraph can be found below throughout this disclosure.

With continued reference to FIG. 1, system 100 includes at least an adapted nutrimental request 124 generated by a user-client device 104. A user-client device 104 may transmit at least an adapted nutrimental request 124 to the at least a central network 108 by receiving the at least a first filter set 120, displaying the at least a first filter set 120, displaying at least a first restricted nutrimental object as a function of a selection from the at least a first filter set 120, and generating the at least an adapted nutrimental request 124 as a function of a selection from the at least a first restricted nutrimental object. Upon receiving the at least a first filter set 120 by a user-client device 104, the user may select any combination of available filters within the at least a first filter set 120 to restrict the nutrimental artifacts displayed to correlate with such filters on the user-client device 104. Display of the restricted nutrimental artifacts based on the at least a first filter set 120 selection produces "at least a first restricted nutrimental object". Adapted nutrimental request 124, as used herein, is a data structure or any other compilation of data which may include at least an element of user data and at least a nutrimental artifact, the at least an element of user data describing the user, user needs, and/or user preference. At least an adapted nutrimental request may include information accurately describing a set of nutrimental artifacts which may correlate to personal information of a user via restriction requirements and/or preferences associated, which may include, as non-limiting examples: a plurality of restriction requirements related to dietary/nutritional profiles of nutrimental artifacts; factors associated with transporting said nutrimental artifacts such as, but not limited to, scheduling, transport methods, geographical location, distance from the user, and the like; and user information relating to user's name, desired address for delivery, payment type, payment method, and the like. The types of the information able to be uploaded to a user-client device 104 as a restricted nutrimental datum is described in more detail herein below.

With continued reference to FIG. 1, system 100 includes a nutrimental processing module 116 operating on the at least a server 112. Nutrimental processing module 116 may include any hardware or software module. Nutrimental processing module 116 is designed and configured to generate at least a first filter set 120 as a function of the at least a restricted nutrimental datum and transmit the at least a first filter set 120 to a user-client device 104. "First filter set" 120, as used herein, includes restriction filters generated as a function of personal information uploaded to a user-client device 104 and contained within at least a restricted nutrimental datum which allow a user to modify/limit/restrict nutrimental artifacts displayed on user-client device 104. Nutrimental processing module 116 may append to a database which contains dietary and/or nutritional filters the nutrimental processing module 116 may use for generation of the at least a first filter set 120; wherein personal information in the at least a restricted nutrimental datum may correspond with a dietary and/or nutritional filter, such as high blood pressure being associated with a decreased sodium filter and decreased fat filter to allow a user to limit available nutrimental artifacts with such parameters. Corresponding or matching of the at least a restricted nutrimental datum with a dietary and/or nutritional filter in a database may be performed with mathematical algorithms, loss functions, and/or machine learning processes as described in more detail below, in reference to FIG. 6. As a non-limiting example, a user may upload, on the user-client device 104, a slew of information from blood test results wherein nutrimental processing module 116 analyzes the results to reflect an allergy to peanuts, high blood cholesterol levels, and a high blood sodium level, wherein nutrimental processing module 116 then generates at least a first filter set 120 which may allow a user to filter out nutrimental artifacts displayed on the user-client device 104 that contain peanuts, are high in cholesterol, and/or are high in sodium. A more detailed description of the types of personal information able to be uploaded by a user to the at least a restricted nutrimental datum to generate the at least a first filter set 120 is described in more detail in reference to FIG. 2.

With continued reference to FIG. 1, system 100 includes a nourishment provider module 128 operating on at least a server 112. Nourishment provider module 128 includes any hardware or software module. Nourishment provider module 128 is designed and configured to receive at least an adapted nutrimental request 124, receive at least a sustenance provider datum 132 and at least a physical performer datum 136, generate at least a sustenance provider instruction set 140 and at least a physical performer instruction set 144 as a function of the at least a sustenance provider datum 132, the at least a physical performer datum 136, and the at least an adapted nutrimental request 124, select the at least a sustenance provider and the at least a physical performer as a function of the at least a sustenance provider instruction set 140 and the at least a physical performer instruction set 144, and transmit the selection of the at least a sustenance provider and the at least a physical performer to a user-client device 104.

With continued reference to FIG. 1, nourishment provider module receives at least an adapted nutrimental request, which may include any of the adapted nutrimental requests as described herein. Nourishment provider module 128 receives at least a sustenance provider datum 132. "Sustenance provider datum" 132 as used herein, is any element of data describing a sustenance provider. "Sustenance provider," as described herein, is an entity that performs the preparation of a nutrimental artifacts. A sustenance provider may include; a privately-owned restaurant, a chain restaurant that is located at multiple locations, a grocery store that prepares meals, a restaurant within a grocery store, a chef or cook who prepares meals at home or in a private commercialized kitchen, a chef or cook who prepares meals in a school or kitchen or space that the chef or cook rents out, a café, or the like. Sustenance provider datum 132 may include for example, a sustenance provider's ability to prepare nutrimental artifacts with certain limitations, such as for example nutrimental artifacts for a certain dietary restriction or preference such as those imposed within the at least an adapted nutrimental request 124, the sustenance provider's preference to prepare nutrimental artifacts within a certain geographical location, and/or an average range for the cost of prepared nutrimental artifacts by the sustenance provider. Sustenance providers may execute a provider performance. A "provider performance" as used herein includes any action involved in the preparation of and/or pursuant to a nutrimental artifact. A provider performance may include the ability for preparation of a nutrimental artifact that adheres to an at least an adapted nutrimental request 124 from a user, for example preparing gluten free meals for a user for a week.

With continued reference to FIG. 1, system 100 may include a sustenance provider network 148. Sustenance provider network 148 may include participation from any sustenance provider. Sustenance provider may include any of the sustenance providers as described above. Sustenance provider network 148 may be used to transmit information such as a sustenance provider instruction set during the selection of at least a sustenance provider. Sustenance provider network 148 may include at least a sustenance provider server which may include any server as disclosed herein throughout this disclosure. The at least a sustenance provider server may include any computing device suitable for use as the at least a server 112. Sustenance provider network 148 may include at least a sustenance provider database which may include any database or datastore structure as disclosed in this disclosure. Although only a single sustenance provider network 148 is depicted, system 100 may be configured to involve multiple sustenance provider networks or various performances within a particular sustenance provider network.

With continued reference to FIG. 1, nourishment provider module 128 receives at least a physical performer datum 136. "Physical performer datum" 136 as used herein, includes any element of data describing the physical performer. "Physical performer" as used herein includes any transportation channel that executes the physical performer instruction set. Physical performer may include an individual operator of a mode of transportation to deliver a nutrimental artifact such as an automobile, bicycle, scooter, boat, bus, airplane, drone, helicopter, train, and the like. Physical performer may execute a physical performance. "Physical performance" as used herein includes any action that is directed at delivering at least a nutrimental artifact. Physical performer may include an individual who works for a ride sharing company such as a taxicab service or a peer to peer ridesharing service. Physical performer may include a common carrier such as air common carriers and ground common carriers. Physical performer may include any grocery delivery service. Physical performer may include any food delivery service. Physical performer datum 136 may include for example, a physical performer's ability to deliver a nutrimental artifact based on requirements within an at least an adapted nutrimental request 124, such as a physical performer's ability to deliver a nutrimental artifact within a certain amount of time, the physical performer's ability to pick up a nutrimental artifact from a sustenance provider within a certain geographical location, the physical performer's ability to deliver a nutrimental artifact to a user located within a certain geographical location or the like. Physical performer instruction set may include any of the physical performer instruction sets as described in more detail herein. Physical performer instruction set is a data structure containing information for physical performer to deliver nutrimental artifact from at least an adapted nutrimental request. Executing the physical performer instruction set may include for example, picking up nutrimental artifact such as a meal from a sustenance provider and delivering the nutrimental artifact to a user. In an embodiment, physical performer may execute a performance by picking up a user nutrimental artifact from a sustenance provider and delivering the nutrimental artifact to the user. In an embodiment, physical performance may be segmented whereby a first physical performer may pick up a user nutrimental artifact from a sustenance provider and deliver the nutrimental artifact to a second physical performer who may deliver the user nutrimental artifact to the user.

With continued reference to FIG. 1, system 100 may include a physical performer network 152. Physical performer network 152 may include any physical performer. Physical performer may include any of the physical performers as described above, including any transportation channel that executes the physical performer instruction set 144. Physical performer network 152 may be used to provide at least a physical performer during the selection of at least a physical performer. Physical performer network 152 may include at least a physical performer server which may include any server as disclosed herein throughout this disclosure. The at least a physical performer server may include any computing device suitable for use as the at least a server 112. Physical performer network 152 may include at least a physical performer database which may include any database or datastore as disclosed in this disclosure. Although only a single physical performer network 152 is depicted, system 100 may be configured to involve multiple physical performer entity networks or various performers within a particular physical performer network.

With continued reference to FIG. 1, nourishment provider module 128 generates at least a sustenance provider instruction set 140 and at least a physical performer instruction set 144 as a function of the at least a sustenance provider datum 132 and the at least a physical performer datum 136 and the at least an adapted nutrimental request 124. "Sustenance provider instruction set" 140 as used herein is a data structure containing information for at least a sustenance provider to prepare nutrimental artifacts requested within at least an adapted nutrimental request 124. Sustenance provider instruction set 140 may include user information including remittance information, preferred remittance methods, one or more physical addresses for a user, contact information such as telephone number and email address, and any other applicable information relating to a user. Sustenance provider instruction set 140 may include one or more user entries containing information such as user preference as to foods and ingredients contained within an adapted nutrimental request such as a preference for a steak to be cooked medium well or for salmon to be prepared in avocado oil. Sustenance provider instruction set 140 may include user entries including information including a user's likes and dislikes regarding preparation of a nutrimental request such as a preference for roasted cauliflower but not boiled cauliflower. Sustenance provider instruction set 140 may include user entries including user selection of a meal and/or meals from a menu provided for by sustenance provider. For example, sustenance provider instruction set 140 may include a specific breakfast user wants prepared such as oatmeal with blueberries from a menu generated by sustenance provider with a choice of five different breakfast options. Sustenance provider instruction set 140 may include information contained within at least an adapted nutrimental request 124 correlating to at least a restricted nutrimental datum and at least a first filter set 120. For example, sustenance provider instruction set 140 may include information such as a user restriction including a user's self-reported allergy to eggs. Sustenance provider instruction set 140 may include a user restriction such as a user's preference for a certain food or meal to contain certain condiments, sauces, and sides, such as for example French fries to be delivered with ketchup or a ham and swiss sandwich to be delivered with mustard. Sustenance provider instruction set 140 may include physical performer information including selected physical performer, contact information of physical performer, mode of transportation of physical performer, identification information as to physical performer such as name, or picture identification and the like. Sustenance provider instruction set 140 may include information such as where and how sustenance provider will hand over possession of nutrimental artifacts from at least an adapted nutrimental request 124 to physical performer.

With continued reference to FIG. 1, "physical performer instruction set" 144, as used herein, is a data structure containing information for physical performer to deliver nutrimental artifact from at least an adapted nutrimental request 124. Physical performer instruction set 144 may include any information pertaining to a user as described above in reference to sustenance provider instruction set 140. Physical performer instruction set 144 may include one or more user entries including for example, a user preference within at least an adapted nutrimental request 124 for nutrimental artifacts to arrive at a certain time, instructions as to what physical performer should do upon delivery such as ring user's doorbell or leave items at user's doorstep. Physical performer instruction set 144 may include sustenance provider information including selected sustenance provider, address of sustenance provider where physical performer will pick up nutrimental artifacts from at least an adapted nutrimental request, contact information for sustenance provider such as phone number and email. Physical performer instruction set 144 may include directions as to how a nutrimental artifacts from at least an adapted nutrimental request should be handled and stored while under care and supervision of physical performer; for example ice-cream may need to be kept on dry ice while a freshly prepared hamburger may need to be kept in an insulated warming tray. Physical performer instruction set 144 may include information and directions as to where physical performer may meet sustenance provider to receive nutrimental artifacts from at least an adapted nutrimental request 124. For example, sustenance provider may prefer for physical performer to wait in executor's mode of transportation upon arrival at sustenance provider's kitchen for example, and sustenance provider may walk outside to executor's mode of transportation and deliver nutrimental artifacts from at least an adapted nutrimental request 124 to executor there. In yet another non-limiting example, sustenance provider may prefer to have executor come inside and pick up nutrimental artifacts from at least an adapted nutrimental request 124 in person.

With continued reference to FIG. 1, nourishment provider module 128 selects at least a sustenance provider and at least a physical performer by generating a loss function of user specific variables and minimizing the loss function. Selection may be performed by a plurality of non-limiting mathematical algorithms, loss functions, and/or machine learning calculations. System 100 may include a selection engine 156 operating on the at least a server 112. Selection engine 156 may include any hardware or software component. In an embodiment, selection engine 156 may perform the selection of the at least a sustenance provider and the at least a physical performer with communication from the nourishment provider module 128 by a plurality of non-limiting mathematical algorithms, loss functions, and/or machine learning calculations. A "variable" as used herein may relate to nutrimental restriction requirements imposed by at least an adapted nutrimental request 124, as they relate to, for example, adapted nutrimental artifacts, sustenance providers, physical performers, and the like. In an embodiment, selection engine 156 may compare one or more sustenance provider options and one or more physical performer options to a mathematical expression representing an optimal combination of user entered variables. Mathematical expression may include a linear combination of variables, weighted by coefficients representing relative importance of each variable in generating an optimal sustenance provider instruction set 140 and an optimal physical performer instruction set 144. For instance, a variable such as total time to delivery may be multiplied by a first coefficient representing the importance of total time to delivery, a second variable such as sustenance provider offerings may be multiplied by a second coefficient representing the importance of sustenance provider offerings, a degree of variance from a physical performer instruction set and/or sustenance provider instruction set may be represented as another parameter, which may be multiplied by an additional coefficient representing an importance of that variable; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

With continued reference to FIG. 1, selecting the at least a sustenance provider and selecting the at least a physical performer may include producing a field of combinations of the at least a sustenance provider and the at least a physical performer and selecting the at least a sustenance provider and selecting the at least a physical performer using a lazy-learning process. A lazy-learning process and/or protocol may be a process whereby machine learning is conducted upon receipt of an input to be converted to an output, by combining the input and training set to derive the algorithm to be used to produce the output on demand. This lazy-learning process may be performed on selection engine 156. In another non-limiting embodiment, such selection processes mentioned herein may be applied to generating at least a first filter set 120, including, for example, generating a loss function of user specific variables and minimizing the loss function. Further mathematical algorithms, loss functions, and/or machine learning processes that may be used by selection engine 156 or other similar devices are described in more detail throughout this disclosure below, especially in relation to FIG. 6.

With continued reference to FIG. 1, nourishment provider module 128 may transmit a selection of the at least a sustenance provider and a selection of at least a physical performer to a user-client device 104. User-client device 104 is configured to receive the selection of the at least a sustenance provider and the selection of the at least a physical performer. Receiving the selected at least a sustenance provider and the selected at least a physical performer may include receiving sufficient data by the user-client device 104 for the user to confirm receipt and acceptance of the at least an adapted nutrimental request, including without limitation, the name and location of the at least a sustenance provider, the name and location of the at least a physical performer, distance from the at least a sustenance provider, total cost associated with the accepted at least an adapted nutrimental request, adapted nutrimental artifacts to be prepared and delivered, and the like. In an embodiment, user-client device 104 may track the progress of the order during the preparation and transport stages of processing should the at least a sustenance provider and the at least a physical performer make such monitoring available.

With continued reference to FIG. 1, nourishment provider module 128 may transmit a subset of data associated with a user/user-client device 104 to at least a sustenance provider and to at least a physical performer upon selecting an at least a sustenance provider and selecting an at least a physical performer. Transmitting the subset of data associated with a user/user-client device 104 to the at least a sustenance provider may include transmitting sufficient data for the sustenance provider to perform the corresponding process, including without limitation all components of the at least an adapted nutrimental request which relate to preparation of adapted nutrimental artifacts as described above and throughout this disclosure, an element of data of a preparation process previously sent from sustenance provider, user name, address of terminal point of delivery, distance from terminal point of delivery, packing instructions, delivery schedule, delivery times, and the like. Transmitting the subset of data associated with a user/user-client device 104 to a physical performer may include transmitting sufficient data for the physical performer to perform the corresponding process, including without limitation all components of the at least an adapted nutrimental request which relate to transfer of adapted nutrimental artifacts as described above and throughout this disclosure, transmitting an element of data indicating selection of a physical transfer process previously sent from physical performer, transmitting an origin point, terminal point, and/or pickup time, user name, distance from terminal point of delivery, packing instructions, delivery schedule, delivery times, specific delivery instructions, and the like. As a further non-limiting example, physical performer may generate its own navigation directions given an origin point and terminal point related a physical performer location and a user delivery address, respectively.

With continued reference to FIG. 1, system 100 may include a group processing module 160 operating on the at least a server 112. Group processing module may include any hardware and/or software module. Group processing module 160 may be designed and configured to receive a plurality of adapted nutrimental requests from a plurality of user-client devices and generate at least an adapted nutrimental request 124 containing at least a group identifier as a function of the plurality of adapted nutrimental requests. Generating the at least an adapted nutrimental request 124 may further include generating at least a second filter set as a function of a plurality of first restricted nutrimental objects and receiving a plurality of adapted nutrimental requests as a functions of a selection from at least a second restricted nutrimental object of the at least a second filter set. At least an adapted nutrimental request 124 may be transmitted in a group ordering schema via group processing module 160 if at least a group identifier accompanies the at least an adapted nutrimental request 124. At least a group identifier may indicate selection by a user on a user-client device for the desire to be part of a group ordering schema which, in an embodiment, may permit a plurality of adapted nutrimental requests from a plurality of user-client devices to be processed together as a single adapted nutrimental request on the at least a server 112. In another embodiment, at least a first restricted nutrimental object may be transmitted in a group ordering schema via group processing module 160 if at least a group identifier accompanies the at least a first restricted nutrimental object. "Group identifier" as used herein indicates selection by a user on a user-client device for the desire to be part of a group ordering schema. In an embodiment, group identifier may permit a plurality of first restricted nutrimental objects from a plurality of user-client devices to be used for generation of at least a second filter set. As a non-limiting example, two coworkers who joined a group ordering schema may each want lunch for three days delivered weekly, one coworker submitting at least an adapted nutrimental request 124 containing only nutrimental artifacts high in protein to meet his fitness goal of muscle gain using his mobile phone and the other coworker submitting at least an adapted nutrimental request 124 containing only nutrimental artifacts that are vegetarian using her mobile phone, wherein both submitted at least an adapted nutrimental requests with group identifiers may be transmitted to a network containing at least a server 112, whereby a group processing module 160 may generate a combined adapted nutrimental request 124 containing a combination of both of the at least an adapted nutrimental requests, wherein the combined adapted nutrimental request 124 may be processed for selection of at least a sustenance provider and at least a physical performer based on being able to meet the needs specified by each user contained within the combined adapted nutrimental request. Another non-limiting example may be where the at least an adapted nutrimental requests submitted by each user in the group ordering schema may be limited by the at least a first restricted nutrimental object of each user-client device 104 in the group ordering schema, wherein using the previous non-limiting example, nutrimental artifacts available for both coworkers may be limited to those that are vegetarian and also high in protein from where each coworker may submit at least an adapted nutrimental request as before. Further details of the group ordering schema and group processing module 160 can be found below in reference to FIG. 12.

Figure 2:
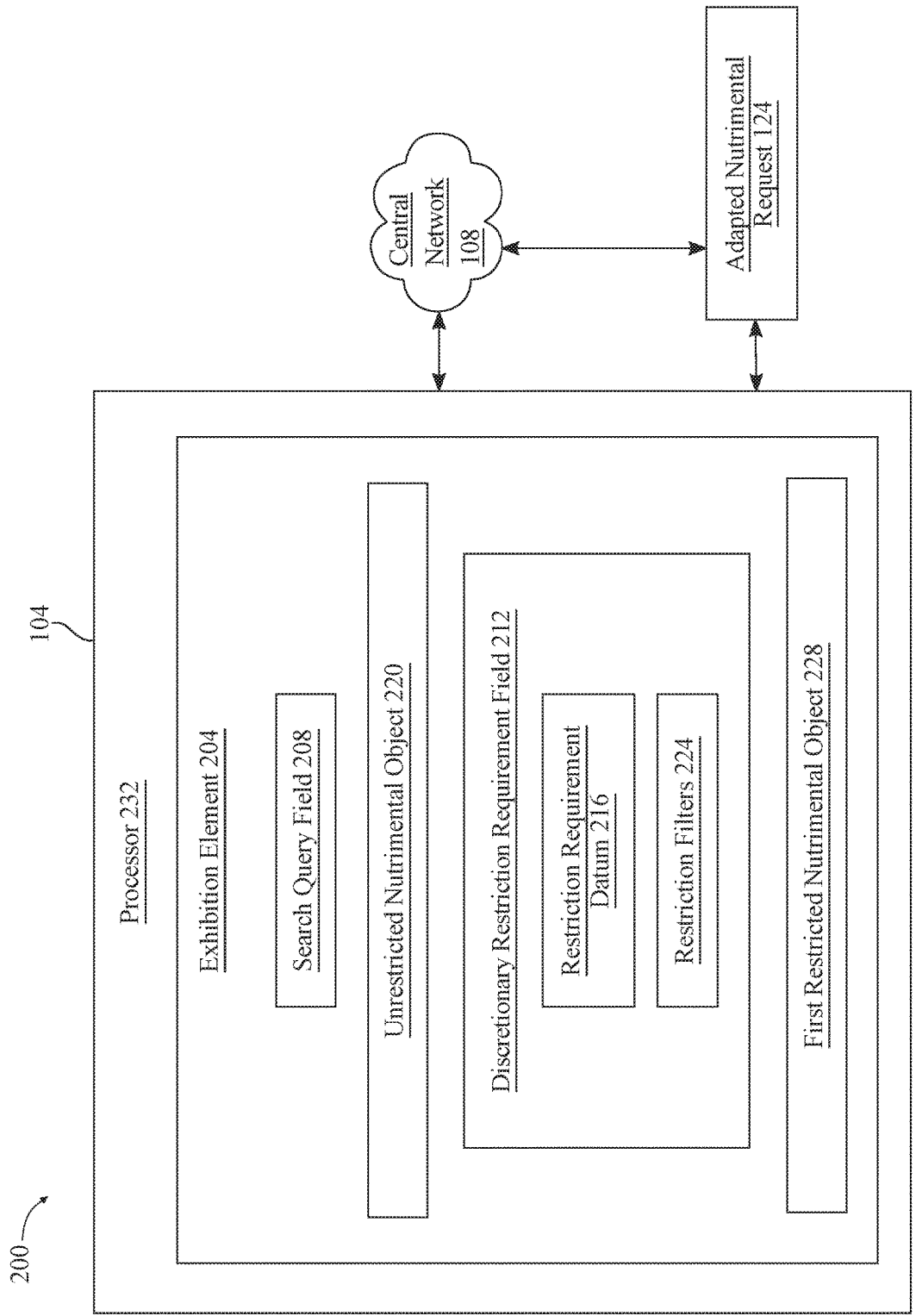
FIG. 2 is a block diagram illustrating an exemplary embodiment of an exhibition elements on a user-client device.

Referring now to FIG. 2, an exemplary embodiment 200 of exhibition element 204 located on a user-client device 104 is illustrated. Exhibition element 204 may include any hardware or software module and as described above in FIG. 1. For example and for illustrative purposes only, user-client device 104 may include an exhibition element 204, or a screen, whereby a user may enter a search query in a search query field 208 to search for nutrimental artifacts available in at least a central network 108. In an embodiment, search query field 208 may include a drop-down menu of choices based on previous user entries. Screen may include a graphical user interface as described above in more detail in reference to FIG. 1. Exhibition element 204 may include a discretionary restriction requirement field 212 where a user may upload at least a restriction requirement datum 216 to manipulate the nutrimental artifacts displayed. Discretionary restriction requirement field 212 may contain categories of restriction requirements a user may select for programmatic upload of personal information associated with such restriction requirement, whereupon this personal information may be transferred to at least a server 112 via at least a central network 108 for storage and/or generation of at least a first filter set 120. At least an unrestricted nutrimental object 220 may be displayed to the user where no data is uploaded to the discretionary restriction requirement field 212. The at least an unrestricted nutrimental object 220 may contain nutrimental artifacts as described above, with no restrictions, allowing the user to enter a search query into the search query field 208 and search for all nutrimental artifacts available on the at least a central network 108. As a non-limiting example, a search query entered into the search query field 208 as used herein includes any search word and/or phrases that a user may enter into a search engine when browsing for a particular nutrimental artifact. A search query may include a word and/or string of words describing a particular category of nutrimental artifacts such as "meals with chicken" or "vegetarian friendly meals." In yet another non-limiting example, a search query may include a word and/or string of words describing a particular product and/or item such as "fried chicken wings" or "steamed broccoli." Submitting such a search query may direct the exhibition element 204 to a new window displaying nutrimental artifacts relating to said search query. A user may manipulate the nutrimental artifacts displayed by uploading of at least a restriction requirement datum 216 to accommodate for personal restrictions and preferences.

With continued reference to FIG. 2, wherein transmitting the at least a restricted nutrimental datum by the user-client device may further include display of a discretionary restriction requirement field 212 and upload of at least a restriction requirement datum 216 to the discretionary restriction requirement field. Uploading of at least a restriction requirement datum 216 to a discretionary restriction requirement field 212 may include personal data related to a user. Personal data may include at least a biological extraction input, at least a well-being input, and/or at least a preference input, as described in more detail below. In an embodiment, transmitting at least a restricted nutrimental datum by a user-client device may include displaying by the user-client device the discretionary restriction requirement field 212 and uploading at least a restriction requirement datum to the discretionary restriction requirement field 212 by a user. User selection of data from the at least a restriction requirement datum 216 to submit for generation of at least a first filter set may include the at least a restricted nutrimental datum, as described above in more detail. At least a restricted nutrimental datum may be transmitted to the at least a central network 108, processed on the at least a server 112, and sent back to the user-client device 104 as at least a first filter set 120. At least a first filter set 120 may be presented/displayed to a user on a user-client device 104 in the form of restriction filters 224.

With continued reference to FIG. 2, upon the user-client device 104 receiving the at least a first filter set 120, restriction filters 224 may be displayed on the exhibition element 204. The restriction filters 224 may include an option for restricting nutrimental artifacts displayed, a non-limiting example being the option to exclude nutrimental artifacts which contain gluten. If this option were selected in this non-limiting example and a search query submitted, then all resulting nutrimental artifacts displayed would be gluten-free. The display of nutrimental artifacts which have a restriction applied are referred to herein as "restricted nutrimental artifacts." Multiple options may also be presented for restricting the nutrimental artifacts displayed, for example, and non-limiting, the option to exclude nutrimental artifacts which contain high salt content, high total fat content, and peanuts. If all three restriction options were selected in this non-limiting example and a search query were submitted, then all resulting nutrimental artifacts displayed would have a lower salt content and lower total fat content than would be displayed without these filters selected, as well as contain no peanuts. Further, as another non-limiting example, an option may be presented for restricting the nutrimental artifacts displayed that relate to a user's goal of weight loss, and if selected may present only nutrimental artifacts upon submission of a search query that are known to be beneficial for weight loss. Restricted nutrimental artifacts that become available and which are displayed in the exhibition element 204 as a result of selection of an option from restriction filters 224 are referred to herein as "at least a first restricted nutrimental object 228."

With continued reference to FIG. 2, a display of at least a first restricted nutrimental object 228 or unrestricted nutrimental object 220 may contain nutritional information associated with such nutrimental artifact. As restriction filters 224 are selected by a user to change which at least a first restricted nutrimental object 228 are displayed, nutritional information may be continuously updated as well. Nutritional information may describe one or more categories of nutrimental objects, such as breakdown by fats, carbohydrates, protein, vegetables, fruits, and the like or nutrition categories such as breakdown by micronutrient such as calcium, Vitamin A, Vitamin D, iron, folate, chromium, and the like; obtaining such information from robust sources such as, for a non-limiting example, the World Health Organization (WHO) Nutrition Landscape Information System which brings together all existing WHO Global Nutrition Databases dynamically, as well as other existing food and nutrition-related data from partner agencies. Input may also include input from experts through exhibition element 204 such as through a graphical user interface. Experts may identify documents as representing good science, good clinical analysis, or the like; experts may identify or enter such documents containing nutrition information relating to nutrimental objects through graphical user interface (GUI).

With continued reference to FIG. 2, a selection from the at least a first restricted nutrimental object 228 allows a user to place an adapted nutrimental request 124 for preparation and transport which may include delivery of the restricted nutrimental artifacts selected from the at least a first restricted nutrimental object 228. In an embodiment, at least an adapted nutrimental request 124 may be generated by the user-client device 104 as a function of the selection from the at least a first restricted nutrimental object 228. Following, the at least an adapted nutrimental request 124 may be transmitted to the at least a central network 108 wherein a nourishment provider module 128 in communication with the at least a central network 108 receives the at least an adapted nutrimental request 124, and processes the at least an adapted nutrimental request 124 to select a sustenance provider to prepare the selected restricted nutrimental artifacts and a physical performer to deliver the restricted nutrimental artifacts once prepared to the user. The nourishment provider module 128 may transmit the selection of the sustenance provider and the physical performer to the user-client device 104, selection details of which can be found throughout this disclosure herein in relation to mathematical algorithms, loss functions, and/or machine learning processes.

Continuing to refer to FIG. 2, the at least a restriction requirement datum 216 may be configured to record at least a biological extraction input. At least a biological extraction input may include any element and/or elements of physiological test results. Test results as used herein may relate to diagnostic test results given by medical professionals, data reported by wearable monitoring devices, and the like. At least a biological extraction input may be from a physically extracted sample, which as used herein, includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. As a further non-limiting example, at least a biological extraction input may include test results from at least a genetic sample. At least a genetic sample may include a complete genome of a person or any portion thereof. At least a genetic sample may include a DNA sample and/or an RNA sample. At least a biological extraction input may include test results from an epigenetic sample, a proteomic sample, a tissue sample, a biopsy, and/or any other physically extracted sample. At least a biological extraction input may include test results from an endocrinal sample. As a further non-limiting example, the at least a biological extraction input may include test results from a signal from at least a sensor configured to detect physiological data of a user and recording the at least a biological extraction input as a function of the signal results. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmo graphic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data. At least a wearable and/or mobile device sensor may detect heart rate or the like. At least a sensor may detect any hematological parameter including blood oxygen level, pulse rate, heart rate, pulse rhythm, blood sugar, and/or blood pressure. At least a sensor may be configured to detect internal and/or external biomarkers and/or readings. At least a sensor may be a part of a system or may be a separate device in communication with a system.

Still referring to FIG. 2, at least a biological extraction input may include test results from any data suitable for use as physiological state data as described above, and further including without limitation any result of any other medical test, physiological assessment, cognitive assessment, psychological assessment, or the like. Restriction filters 224 presented based on the at least a biological extraction input may include, without limitation, nutritional content, food and/or food groups to consume or avoid, dietary recommendations that may reverse a deficiency of a nutrient, digestibility, ideal nutrition choices for a user, and the like. User-client device 104 may receive at least a biological extraction input from one or more other devices after performance. As a non-limiting example, at least a biological extraction input may include, as a non-limiting example, reported results from a complete metabolic panel, a frequently ordered panel of 14 tests that gives a healthcare provider important information about the current status of a person's metabolism, from a user's blood sample; wherein any abnormalities may dictate the generation of at least a first filter set. Continuing the non-limiting example, if the sodium levels reported in this complete metabolic panel are high at least a first filter set may be generated allowing the user to restrict themselves to only viewing nutrimental artifacts which are low in sodium. As a continued non-limiting example, the user may also upload lipid panel blood results, wherein if total cholesterol reported is high at least a first filter set may be generated containing filters which allow the user to filter out high sodium and/or high cholesterol nutrimental artifacts. Persons skilled in the art, upon reviewing the entirety of this disclosure, will be aware of various additional examples of at least a physiological test result or other test results consistent with this disclosure which may be uploaded as a biological extraction input.

Continuing to refer to FIG. 2, the at least a restriction requirement datum 216 may be configured to record at least a well-being input. At least a well-being input may include, without limitation, exercise programs including amount, intensity, and/or types of exercise, calorie limitations, desired weight, desired nutrients, and the like. At least a well-being input may include, without limitation, dietary or nutritional goals based on data including nutritional content, digestibility, or the like. At least a well-being input may include a request for a particular diet, food, ingredient, food group, nutrition plan, style of eating, lifestyle, and/or nutrition to meet a well-being goal. A well-being goal may be a user's desire to lose weight, gain weight, gain muscle, get a more restful sleep, increase stamina, increase alertness, and the like. At least a well-being input may include a request for a particular type of diet such as Atkins, Paleo, Whole 30, gluten free, ketogenic, dairy free, Mediterranean, soy free, and the like to meet a well-being goal. At least a well-being input may be presented back to the user based on, without limitation, nutritional content, food and/or food groups to consume or avoid, dietary recommendations that may help achieve a well-being goal, ideal nutrition choices for a well-being goal, and the like; a specific non-limiting example being an option in the restriction filters 224 for high protein and high carbohydrate nutrimental artifacts based on well-being goal of weight and muscle gain in the at least a well-being input. Persons skilled in the art, upon reviewing the entirety of this disclosure, will be aware of various processes that may be used as well-being inputs consistently with this disclosure.

Continuing to refer to FIG. 2, the at least a restriction requirement datum 216 may be configured to record at least a preference input. At least a preference input may include a terminal location for delivery of a restricted nutrimental artifact. "Terminal location," as used in this disclosure, is a location to which a restricted nutrimental artifact is to be physically transferred; as a non-limiting example, at least an adapted nutrimental request 124 may include, as a terminal location, a current or likely future location of a user submitting the request, along with a description of a restricted nutrimental artifact, which may include a meal, set of meals, set of ingredients, or the like which the user is requesting be physically transferred to the terminal location. Further, a user may enter a geographic restriction into the at least a preference input that relates to a terminal location; as a non-limiting example, a user may submits a requirement to the at least a preference input for the sustenance provider to be located within twenty miles of the terminal location, a restriction that will be considered when selecting a sustenance provider and a physical performer, possibly being performed with mathematical algorithms, loss functions, and/or machine learning processes as described throughout this disclosure herein below.

With continued reference to FIG. 2, an at least a preference input may include a nutrimental allocation standard. Nutrimental allocation standard as used herein, is a user input containing a total amount of resources that a user is willing to devote to nutrimental artifacts. Resources may include a budget, and/or total dollar amount that a user may devote to the restricted nutrimental artifact for a specific period of time. For example, and non-limiting, a user may enter a total budget amount that a user is willing to spend on himself or herself for a month's worth of nutrimental artifacts. In an embodiment, a user may enter a total budget amount for any timeframe. In an embodiment, user may allocate a certain dollar amount to each meal evenly in a given timeframe to allocate a certain dollar amount to individuals meals in an order containing multiple restricted nutrimental artifacts. In an embodiment, entering a nutrimental allocation standard into the at least a preferred input may create a restriction when selection of sustenance provider and physical performer is occurring. A non-limiting example could be when a user enters a nutrimental allocation standard of $10 per meal for ten meals to be delivered the following week; wherein a selected sustenance provider and physical performer must accept these and other restriction terms presented in the adapted nutrimental request 124, though exceptions may be had when implementing mathematical algorithms, loss functions, and/or machine learning processes for the selection techniques mentioned herein.

With continued reference to FIG. 2, an at least a preference input may include a specific request for a particular diet, food, ingredient, food group, nutrition plan, style of eating, lifestyle, and/or nutrition, based on personal preference or knowledge by a user, for generating specific restricted nutrimental artifacts as a function of at least a first filter set. At least a preference input may include elimination of certain foods or food groups because of a dislike for such foods, an allergy to a food, and/or a sensitivity. For example, at least a preference input may include a request for egg free nutrimental artifacts based on a user's aversion to eggs. In yet another non-limiting example, at least a preference input may include a request for nutrimental artifacts free of bell peppers because of a user's known previous food sensitivity. At least a preference input may include a request for nutrimental artifacts free of shellfish because of a user's known allergic response to shellfish. At least a preference input may include a request for display of nutrimental artifacts based on religious or moral beliefs such as kosher diet or vegetarian diet. At least a preference input may include a request to eliminate certain food groups such as grain for grain-free nutrimental artifacts. At least a preference input may include a request to eliminate certain ingredients that may be commonly found in food such as a request for nutrimental artifacts free of monosodium glutamate (MSG) or corn starch. At least a preference input may include a request for a certain level or quality of ingredients such as locally sourced ingredients, free range meats, wild caught fish, organic produce and the like. At least a preference input may include a request for certain nutrimental artifacts because of a previously diagnosed medical condition, such as a user who has been previously diagnosed with diabetes type 2 and is following a low sugar diet. At least a preference input may include a preference input based on a certain style of eating that a user prefers, such as low carb, high protein, low fat, and the like. At least a preference input may include a preference input as a function of a medication, supplementation, and/or medical treatment or therapy that a user may be undergoing. For example, a user currently taking a medication such as metronidazole may submit at least a preference input for nutrimental artifacts free of alcohol, while a user currently supplementing with zinc may submit at least a preference input for nutrimental artifacts free of oysters. At least a preference input may include at least a request to be implemented in the at least an adapted nutrimental request for one meal, a specific number of meals such as three meals, or a certain number of meals over a predetermined time period such as a week's worth of meals. At least a preference input may include a request for specific types of meals such as three breakfasts, fives lunches, and fives dinners. Meal types and meal numbers ordered may be customized based on user inputs and user reported eating habits. For example, a user who routinely does not eat breakfast may submit a preference input for no breakfast meals, while a user who habitually eats breakfast may submit a preference input for breakfast, lunch, and dinner meals.

With continued reference to FIG. 2, an at least a preference input may include any other user restriction requirement not falling under biological extraction or well-being input restrictions of the at least a restriction requirement datum 216. Dietary and/or nutritional parameters presented based on the at least a preference input may include, without limitation, nutritional content, food and/or food group to consume or avoid, dietary recommendations that may reverse a deficiency of a nutrient, ideal nutrition choices for a user, digestibility, specific preparation instructions, and the like; a specific non-limiting example being an option in the restriction filters 224 for gluten-free nutrimental artifacts and foods able to be cooked in grapeseed oil based on the input for the desire to avoid foods containing gluten and the input for the preferred taste of foods cooked in grapeseed oil in the at least a preference input.

Continuing to refer to FIG. 2, the at least a first filter set 120 may be configured to include at least a body intolerability score. At least a body intolerability score may be a graded scale relating to, for example, allergic reactions to any of the nutrimental restrictions in at least a first filter set 120. Allergic reactions may include Type 1 immunoglobulin E (IGE) reactions, Type 2 cytotoxic reaction, type 3 immune complex reaction, type 4 cell-mediated reactions, immunoglobulin G (IGG) reactions, immunoglobulin M (IGM) reactions, food intolerances, and the like. Body intolerability score may be represented on a continuum, whereby a scale of 1 to 10 may be used to indicate a user's level of allergic response to a given nutrimental object. For example, a user self-reported score of 1 may indicate a very mild intolerance that produces symptoms such as mild gastrointestinal discomfort whereas a score of 10 may include a highly allergic response such as anaphylaxis that requires medications such as epinephrine and/or Benadryl to reverse the effects of. In a non-limiting example, a user may have reported to a restricted nutrimental datum an allergy applies, so an option to filter out foods with apples appears in the at least a first filter set 120, but wherein a user has a very minor allergic reaction to apples and doesn't mind eating them they may set a body intolerability score to "3 out of 10" to display foods that do have some apples but maybe not foods which have apples as the main ingredient. In another non-limiting example, if a user reported a deathly allergic reaction to peanuts, they may set a body intolerability score to "10 out of 10" to completely eliminate foods which contain even a trace amount of peanuts. In a non-limiting embodiment, the display of adapted nutrimental artifacts based on body intolerability scores may be determined by a mathematical expression representing an optimal combination of body intolerability score parameters such as a linear combination of parameters, weighted by coefficients representing relative importance of each parameter. A more detailed description of this mathematical expression and other non-limiting mathematical algorithms, loss functions, and/or machine learning processes as described in more detail in reference to FIG. 6.

Continuing to refer to FIG. 2, the at least a first filter set 120 may be configured to include at least a user aversion score. At least a user aversion score may be a graded scale relating to, for example, a user's personal preference of any of the nutrimental restrictions in at least a first filter set 120. As a non-limiting example, a user may have a strong distaste for broccoli and a strong liking for beets, and so may set a user aversion score within at least a first filter set 120 as "preference for broccoli: 0 out of 10" and "preference for beets: 10 out of 10", thus displaying to the user food that contain no broccoli and foods that contain beets as the main ingredient first. In a broad non-limiting example, a user may set a user aversion score in relation to types of cuisine such as Italian, Indian, Caribbean, Latin American, and the like, to categories of food such as grains, leafy greens, poultry, beef, citrus fruits, and the like, to preferred tastes such as salty, sweet, sour, bitter, and the like, or any other type of category nutrimental artifacts may be categorized by. In a non-limiting embodiment, the display of adapted nutrimental artifacts based on user aversion scores may be determined by a mathematical expression representing an optimal combination of user aversion score parameters such as a linear combination of parameters, weighted by coefficients representing relative importance of each parameter. A more detailed description of this mathematical expression and other non-limiting mathematical algorithms, loss functions, and/or machine learning processes as described in more detail in reference to FIG. 6.

Referring now to FIG. 3, an exemplary embodiment 300 of nutrimental objects are illustrated. Unrestricted nutrimental object 304 may include a list of nutrimental artifacts that may be displayed to a user such as on exhibition element 204. Unrestricted nutrimental object 304 may be categorized by categories, including for example by meal type, meal course, meal selection and the like. Unrestricted nutrimental object 304 may be unrestricted, whereby all products available to a user may be displayed. Unrestricted nutrimental objects may include all possible nutrimental objects that may be available to a user in system 100. As a non-limiting example, unrestricted nutrimental object 304 displays all available nutrimental artifacts classified as desserts that may be available to a user in system 100 that a user may select. A restricted nutrimental object 308 may be any restricted nutrimental object as described throughout the entirety of this disclosure herein. Restricted nutrimental object 308 may be categorized by categories, including for example by meal type, meal course, meal selection and the like. Restricted nutrimental object 308 may display a list of adapted nutrimental artifacts based on a selection of at least a first filter set. Restricted nutrimental objects may include all possible nutrimental objects that correspond to a selection of at least a first filter set that may be available to a user in system 100. As a non-limiting example, unrestricted nutrimental object 304 may be restricted whereby a user may enter a preference such as to not consume chocolate whereby desserts containing chocolate may be removed and not displayed to a user. In such an instance, restricted nutrimental object 308 is produced which may eliminate desserts containing chocolate including chocolate brownies, chocolate cake, chocolate chip cookies, chocolate fudge, and chocolate pudding. In a further embodiment, restricted nutrimental object 308 may display further restricted nutrimental artifacts whereby a user who may be allergic to apples may have desserts removed from view that do not contain apple including apple pie and apple fritter. All of the restricted nutrimental objects not found on list 308 are located on unrestricted nutrimental object list 304.

Referring now to FIG. 4, an exemplary embodiment of a display 400 is illustrated. Display may include a display visible to a user at exhibition element 204. Display 400 may include a user preference table 404 whereby user preferences may have been entered as at least a preference input, as described above, for certain meals and meal selections. Preferences may include for example, a maximum price per meal that a user may be willing to spend on any given meal, a maximum distance and location to travel and a preference for who may be preparing a meal. For example, a user may enter a preference for meals that include lamb, chicken, and duck with all accompanying sides. Nutrimental display 408 may contain a list of meals that may be displayed to a user based on user entered preferences. In an embodiment, meals may include nutritional information such as portion, total protein, total carbohydrates, total fat, total cholesterol, total iron, and total sodium level. Information contained within nutrimental display 408 may be based on user preferences 404. In an embodiment, preferences entered by a user in preferences 404 may be utilized by system 100 to display meals 400 to a user. In an embodiment, a user preference entry that contains at least a first restricted nutrimental object that only contains restriction requirements relating to preference inputs mentioned within the preference table 404 are illustrated.

Referring now to FIG. 5, an exemplary embodiment of a display 500 is illustrated. Display 500 may include a user preference table 504 whereby user preferences may have been entered as at least a preference input, as described above, for certain meals and meal selections. In an embodiment, user preference table 504 may display information from a preference input such as user desired price per meal, distance of sustenance provider from user, preferred supplemental provider type such a home chef over a restaurant, and how many meals per person. In an embodiment, nutrimental display 508 may display a preferred input which may have included, for example, a specific oil type that a user may prefer to have a meal cooked in. Nutrimental display 508 may include a display of a well-being input that may include an elimination of certain foods based on a personal health goal such as a preference to eliminate fried foods because of a weight loss goal. In an embodiment, nutrimental display 508 may include a display of a biological extraction input that may include test results from an analysis of genetic testing, such as a diagnosis of celiac disease that may result in foods free of gluten. Nutrimental display 508 may contain a list of meals that may be displayed to a user as a function of user preferences/restriction requirements. For example, nutrimental display 508 that contains a well-being input for food to be cooked in grapeseed oil may display only meals that can be prepared and cooked in grapeseed oil, whereby meals that cannot be prepared in grapeseed oil may not be displayed to a user. The restriction requirements mentioned herein in reference to FIG. 5 are meant to limit those meals displayed in FIG. 4, giving an exemplary non-limiting example of how filters pertaining to restriction requirements may be utilized.

Figure 6:
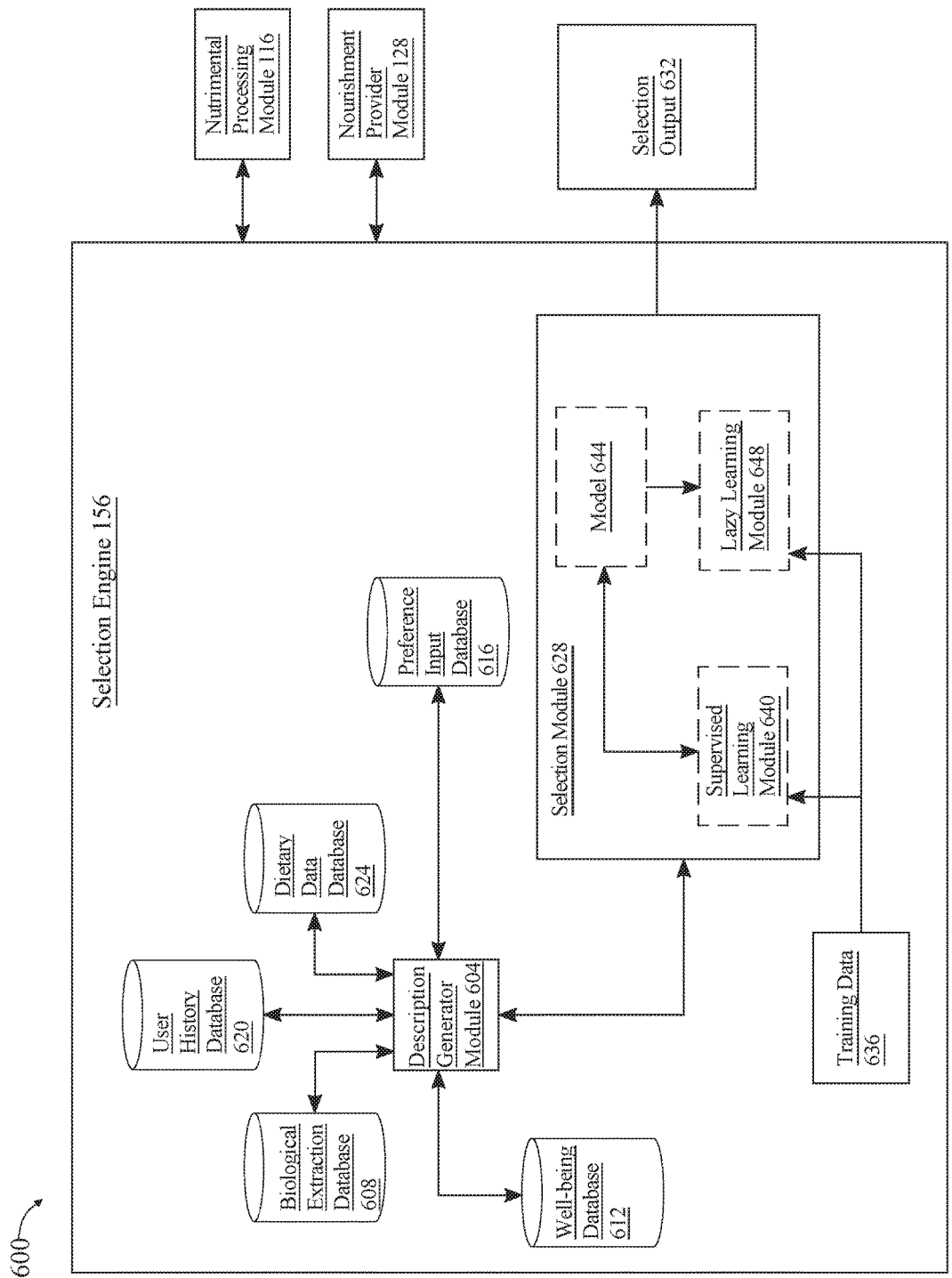
FIG. 6 is a block diagram illustrating an exemplary embodiment of a selection engine system operation on a server.

Referring now to FIG. 6, an exemplary embodiment 600 of selection engine 156 is illustrated. Selection engine 156 may select the at least a sustenance provider and select the at least a physical performer by generating a loss function of specific variables and minimizing the loss function. Selection engine 156 may select the at least a sustenance provider and select the at least a physical performer by producing a field of combinations of the at least a sustenance provider and the at least a physical performer and selecting the at least a sustenance provider and selecting the at least a physical performer using lazy-learning process.

With continued reference to FIG. 6, selection engine 156 may include a description generator module 604 operating on the at least a server 112. Description generator module 604 may include any suitable hardware and/or software module as described in this disclosure. Description generator module 604 may communicate with nutrimental processing module 116 for generating at least a first filter set and/or nourishment provider module 128 for selecting at least a sustenance provider and selecting at least a physical performer. Description generator module 604 is designed and configured to generate a plurality of nutrimental transfer descriptors. A nutrimental transfer descriptor, as used herein, is any element of data which describes at least (1) a nutrimental artifact within at least an adapted nutrimental request, (2) a plurality of information related to at least a restricted nutrimental datum, at least a sustenance provider, and at least a physical performer, and (3) at least a parameter of a physical transfer process bringing the at least a nutrimental artifact to the terminal location specified in the at least an adapted nutrimental request. Each nutrimental transfer descriptor may describe a physical transfer process, of a plurality of physical transfer processes, to be performed by a corresponding physical performer of a plurality of physical performers. Each nutrimental transfer descriptor describes at least an adapted nutrimental artifact of at least an adapted nutrimental request to be provided during a corresponding physical transfer process. As an additional non-limiting example, provided nutrimental transfer descriptor may match an adapted nutrimental artifact previously requested and/or received by user; such a previously requested and/or received at least a restricted nutrimental artifact may be recorded in a database. Further, databases may be accessed and used for matching at least a restricted nutrimental object to a filter for generating at least a first filter set, selecting at least a sustenance provider, and/or selecting at least a physical performer, as discussed below.

Continuing to refer to FIG. 6, selection engine 156 may be configured to receive at least a restricted nutrimental datum from nourishment provider module 128 to generate at least a first filter set for display on a user-client device as a function of the at least a restricted nutrimental datum originally transmitted by a user-client device. Selection engine 156 may use nutrimental transfer descriptors mentioned throughout this disclosure to compare relevant information to a nutrimental reference set. "Nutrimental reference set" as used herein includes a data structure containing information for determining, for example, which filter set to generate as a function of information related to restricted nutrimental data in a nutrimental transfer descriptor, wherein a nutrimental reference set may be a multitude of different databases depending on the information contained within the restricted nutrimental data of a nutrimental transfer descriptor. In an embodiment, selection engine 156 may compare elements of a nutrimental transfer descriptor to databases, being the nutrimental reference sets, including, but non-limiting: biological extraction database 608, well-being database 612, preference input database 616, user history database 620, and dietary data database 624. In an embodiment, databases mention herein may include any data structure for ordered storage and retrieval of data, which may be implemented as a hardware or software module. A database may be implemented, without limitation, as a relational database, a key-value retrieval datastore such as a NOSQL database, or any other format or structure for use as a datastore that a person skilled in the art would recognize as suitable upon review of the entirety of this disclosure. A database may include a plurality of data entries and/or records corresponding to adapted nutrimental artifacts or information needed to create at least a first filter set as described herein. Data entries and/or records may describe, without limitation, data describing one or more potential ingredient sets and/or preparation processes associated with an adapted nutrimental artifact. Data entries in a database may be flagged with or linked to one or more additional elements of information, which may be reflected in data entry cells and/or in linked tables such as tables related by one or more indices in a relational database; one or more additional elements of information may include data describing regional, geographic, and/or other extant variations in ingredients and/or preparation techniques relating to listed at least an adapted nutrimental request. Persons skilled in the art, upon reviewing the entirety of this disclosure, will be aware of various ways in which data entries in referred to databases may reflect categories, cohorts, and/or populations of data consistently with this disclosure.

With continued reference to FIG. 6, description generator module 604 may generate one or more physical transfer processes by communicating with one or more physical performers. For instance, and without limitation, description generator module 604 may transmit, to each physical performer of a plurality of physical performers, information describing the at least an adapted nutrimental request 124; information may include, without limitation, an origin point and terminal point. Each physical performer may transmit to the at least a server 112, path information for one or more vehicles of physical performer. Path information may include, without limitation, a current location of a vehicle, a current heading or direction of travel of the vehicle, one or more future stops at which the vehicle is currently scheduled to stop, and/or one or more paths the vehicle is likely to travel. In an embodiment, physical performer may receive only a request to describe such vehicles, and may send only such path information; alternatively, where description generator module 604 has transmitted origin point and/or terminal point, physical performer may send one or more potential paths that one or more vehicles may be able to traverse between origin point and terminal point. In an embodiment, prospective paths may be calculated based on estimated time of production of a restricted nutrimental artifact; for instance a collation may take 20 minutes from request to be completed, and physical performer may estimate likely ability of one or more vehicles to arrive at or near to the time of completion. In an embodiment, time until completion of a restricted nutrimental artifact is provided by the at least a server 112 corresponding to the entity preparing the restricted nutrimental artifact of the at least an adapted nutrimental request; alternatively or additionally, description generator may determine an average amount of time a given restricted nutrimental artifact takes to be completed at a given entity, and use the determined average amount of time to determine a likely time of completion.

Alternatively or additionally, and still viewing FIG. 6, description generator module 604 may generate estimated paths for one or more vehicles given report positions for each of the one or more vehicles, origin point, and terminal location; persons skilled in the art will be aware of various ways in which estimated paths may be generated. A generated path may depend on another generated path; for instance, a potential or selected path from a first origin point to a first terminal point may include at least a segment of a path from a second origin point to a second terminal point, and description generator module 604 may generate potential paths for each assuming that the other path has or has not been chosen. As a non-limiting example, where two potential paths having shared segments are presented to two or more users sharing a terminal point, description generator module 604 may provide the two users with at least a nutrimental transfer descriptor including a shared route as a possible selection for the two users.

Continuing to refer to FIG. 6, generation of each nutrimental transfer descriptor of at least a nutrimental adaptation request may include combination of restricted nutrimental artifacts of at least a restricted nutrimental request identified as described above with a physical transfer process of at least a physical transfer process; this may generate a large number of nutrimental transfer descriptors, as each restricted nutrimental artifact may have multiple potential paths for its delivery, and there may be a large quantity of restricted nutrimental artifacts that may potentially match the at last an adapted nutrimental request 124. This initial set of candidates may be chosen within a geographical/travel time threshold; for instance, any path having a length above a threshold amount, a travel time above a threshold amount, and/or a length and/or time exceeding an average travel time and/or length of paths generated by more than a threshold amount. Similarly, origin points more than a threshold geographical distance and/or travel time away from terminal point may be eliminated from generated nutrimental transfer descriptors. Each threshold may be established as a default value and/or selected by a user; any threshold may be user specific.

Still referring to FIG. 6, each nutrimental transfer descriptor further includes a plurality of attributes, each attribute corresponding to a selection criterion of a plurality of selection criteria. Each attribute may include a degree of variance from an element of nutrimental request, which element may be described here for the sake of brevity as a "requested element"; for instance, a first attribute may represent a degree to which a sustenance provider ingredient list differs from a requested ingredient list, a higher number representing a greater number of divergent ingredients, while at least second attribute may represent a degree to which an ingredient list differs from the at least a nutrimental restriction data within the at least a nutrimental request, and a third attribute may represent a degree to which a physical transfer process of a nutrimental transfer descriptor differs from an ideal or optimal travel distance of time. Each degree of variance may include either a degree to which a provided value differs from the requested value, a degree to which the exact variance is unknown, or both; for instance, where not all ingredients are known, a degree of variance from requested ingredients may be estimated based on a typical recipe, and/or assumed to be high. Similarly, a route calculated as a physical transfer process that has a certain travel time, but also a certain degree of uncertainty in that travel time, may be calculated as having a higher degree of variance than a route having a lesser degree of uncertainty from the same travel time. Persons skilled in the art, upon reviewing the entirety of this disclosure, will be aware of various attributes that may be calculated or derived with regard to various elements of nutrimental transfer descriptors as compared to various elements of the at least an adapted nutrimental request 124; generally, an attribute may be generated to reflect a degree of variance from any option a user may have selected with at least an adapted nutrimental request 124.

Continuing to refer to FIG. 6, system 600 includes a selection module 628 operating on the selection engine 156. Selection module 628 may include any suitable hardware module and/or software module as described in this disclosure. Selection module 628 designed and configured to select a nutrimental transfer descriptor of the plurality of nutrimental transfer descriptors by executing a selection function on the plurality of nutrimental transfer descriptors. As used herein, a "selection function" is a function that generates a selection output 632 as a function of the plurality of selection criteria, plurality of attributes, and restriction requirements; a "selection output" as used herein is an output that orders a plurality of nutrimental transfer descriptors according to a degree of desirability or optimization given selection criteria. As a non-limiting example, selection function may rank all nutrimental transfer descriptors according to each attribute, calculate an average ranking across attributes per nutrimental transfer descriptor, where average may include any form of average including without limitation arithmetic mean and/or geometric mean, and/or rank all nutrimental transfer descriptors according to attribute-wise ranking and/or average ranking. Selection function may, for instance display only a highest-ranking option or a certain number of highest-ranking options to a user; alternatively, selection function may display a plurality, or all options with rankings according to one or more criteria, ordered by average ranking, one or more per-criteria rankings, or any other ranking as described in this disclosure. A user may be able to select which ranking according to which nutrimental transfer descriptors are ranked, or a ranking may be selected by default, all in relation to the at least a nutrimental adaptation request.

With continued reference to FIG. 6, in an embodiment, selection function used by nourishment provider module 128 may compare one or more nutrimental transfer descriptors to a mathematical expression representing an optimal combination of nutrimental provision parameters. Mathematical expression may include a linear combination of parameters, weighted by coefficients representing relative importance of each parameter in generating an optimal nutrimental transfer descriptor. For instance, a total transit time in seconds of a nutrimental transfer descriptor may be multiplied by a first coefficient representing the importance of total transit time, a total cost of a nutrimental transfer descriptor may be multiplied by a second coefficient representing the importance of cost, individual scores of at least a body intolerability score may be multiplied by another coefficient representing the importance of a score, individual scores of at least a user aversion score may be multiplied by another coefficient representing the importance of a score, a degree of variance from a nutrimental restriction requirement of an adapted nutrimental request may be represented as another parameter, which may be multiplied by another coefficient representing the importance of that parameter, a degree of variance from a requested recipe may be multiplied by an additional coefficient representing an importance of that parameter, and/or a parameter representing a degree of variance from one or more dietary restrictions may be provided a coefficient representing the importance of such a variance; persons skilled in the art, upon reviewing the entirety of this disclosure, will be aware of various parameters that may be weighted by various coefficients. Use of a linear combination is provided only as an illustrative example; other mathematical expressions may alternatively or additionally be used, including without limitation higher-order polynomial expressions or the like.

Still viewing FIG. 6, mathematical expression may represent a loss function, where a "loss function" is an expression an output of which an optimization algorithm minimizes to generate an optimal result. As a non-limiting example, nourishment provider module 128 may calculate parameters of each of a plurality of nutrimental transfer descriptors, calculate an output of mathematical expression using the parameters, and select a nutrimental transfer descriptor that produces an output having the lowest size, according to a given definition of "size," of the set of outputs representing each of the plurality of nutrimental transfer descriptors; size may, for instance, included absolute value, numerical size, or the like. Selection of different loss functions may result in identification of different nutrimental transfer descriptors as generating minimal outputs; for instance, where transit time is associated in a first loss function with a large coefficient or weight, a nutrimental transfer descriptor having a short transit time may minimize the first loss function, whereas a second loss function wherein transit time has a smaller coefficient but degree of variance from a dietary restriction has a larger coefficient may produce a minimal output for a different nutrimental transfer descriptor having a longer transit time but more closely hewing to a dietary restriction.

Alternatively or additionally, and still referring to FIG. 6, each nutrimental transfer descriptor may be represented by a mathematical expression having the same form as mathematical expression; selection engine 156 may compare the former to the latter using an error function representing average difference between the two mathematical expressions. Error function may, as a non-limiting example, be calculated using the average difference between coefficients corresponding to each parameter. A nutrimental transfer descriptor having a mathematical expression minimizing the error function may be selected, as representing an optimal expression of relative importance of parameters to a system or user. In an embodiment, error function and loss function calculations may be combined; for instance, a nutrimental artifact delivery option resulting in a minimal aggregate expression of error function and loss function, such as a simple addition, arithmetic mean, or the like of the error function with the loss function, may be selected, corresponding to an option that minimizes total variance from optimal parameters while simultaneously minimizing a degree of variance from a set of priorities corresponding to nutrimental transfer descriptor parameters. Coefficients of mathematical expression and/or loss function may be scaled and/or normalized; this may permit comparison and/or error function calculation to be performed without skewing by varied absolute quantities of numbers.

Still referring to FIG. 6, mathematical expression and/or loss function may be provided by receiving one or more user commands. For instance, and without limitation, a graphical user interface may be provided to user with a set of sliders or other user inputs permitting a user to indicate relative and/or absolute importance of each restriction or preference to the user. Sliders or other inputs may be initialized prior to user entry as equal or may be set to default values based on results of any machine-learning processes or combinations thereof as described in further detail below.

With continued reference to FIG. 6, mathematical expression and/or loss function may be generated using a machine learning to produce loss function. For instance, and without limitation, a linear regression process may be performed to generate a linear function of attributes to be used as a loss function as described above. A machine learning process, as used herein is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 636 may include a plurality of data entries, each entry representing a set of data elements that were recorded, received, and/or generated together; data elements may be correlated by shared existence in a given data entry, by proximity in a given data entry, or the like. Multiple data entries in training data 636 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 636 according to various correlations; correlations may indicate causative and/or predictive links between categories of data elements, which may be modeled as relationships such as mathematical relationships by machine-learning processes as described herein. Training data 636 may be formatted and/or organized by categories of data elements, for instance by associating data elements with one or more descriptors corresponding to categories of data elements. As a non-limiting example, training data 636 may include data entered in standardized forms by persons or processes, such that entry of a given data element in a given field in a form may be mapped to one or more descriptors of categories. Elements in training data 636 may be linked to descriptors of categories by tags, tokens, or other data elements; for instance, and without limitation, training data 636 may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 6, training data 636 may include one or more elements that are not categorized; that is, training data 636 may not be formatted or contain descriptors for some elements of data. Machine-learning algorithms and/or other processes may sort training data 636 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a nutrimental artifact name and/or a description of at least a restricted nutrimental datum may be identified by reference to a list, dictionary, database, or other compendium of terms, permitting ad-hoc categorization by machine-learning algorithms, and/or automated association of data in the data entry with descriptors or into a given format. The ability to categorize data entries automatedly may enable the same training data 636 to be made applicable for two or more distinct machine-learning algorithms as described in further detail below.

In an embodiment, and continuing to refer to FIG. 6, training data 636 may be created using a plurality of past user interactions. Past user interactions may include only interactions with a current user; in this case loss function may be user-specific, using a training set composed of past user selections. Such a user-specific training set may initially be seeded using one or more user entries as above. Similarly, user may enter a new command changing mathematical expression, and then subsequent user selections may be used to generate a new training set to modify the new expression. Alternatively or additionally, training data 636 may include past interactions with one or more additional users. One or more additional users may be selected based on similarities to current user; similarities may include, without limitation, one or more similar medical conditions, one or more similar dietary restrictions, one or more demographic similarities, such as age, sex, ethnicity, national origin, language, or the like. As a non-limiting example, selection module 628 may search user history database 620 for users having at least a restriction requirement matching at least a restriction requirement of current user and use history of such users to generate training data 636; this process may alternatively or additionally be used to select all users sharing any other attribute or demographic feature with current user history database 620 and generate training data 636 based on such users' histories. Alternatively or additionally, all users may be used. In a non-limiting example, a first data entry may contain an adapted nutrimental request 124 from a user and a correlated datum to potential sustenance providers or physical performers which may be modified based on the training data say if, for example, user history shows high satisfaction with at home chefs. In an embodiment, selection module 628 may generate a machine-learning model using all users or a selected set of users as described above, and then modify the model using additional training using history of current user. In an embodiment, system 100 may receive training data which may be utilized initially to generate outputs utilizing system 100 before user histories and previous user data may be utilized to generate training data. In such an instance, system 100 may receive a first training set wherein the first training set includes a plurality of first data entries, each first data entry of the first training set including at least an element of restricted nutrimental data and at least a correlated first adapted nutrient request. Restricted nutrimental data may include any of the restricted nutrimental data and/or restricted nutrimental datums as described herein. Adapted nutrient request may include any of the adapted nutrient requests as described herein. First training set may include a plurality of data entries, each entry representing a set of data elements that were recorded, received, and/or generated together; data elements may be correlated by shared existence in a given data entry, by proximity in a given data entry, or the like. Multiple categories of data elements may be related in first training set according to various correlations; correlations may indicate causative and/or predictive links between categories of data elements, which may be modeled as relationships such as mathematical relationships by machine-learning processes as described in further detail below. First training set may be formatted and/or organized by categories of data elements, for instance by associating data elements with one or more descriptors corresponding to categories of data elements. As a non-limiting example, first training set may include data entered in standardized forms by persons processes, such that entry of a given data element in a given field in a form may be mapped to one or more descriptors of categories. Elements in training data may be linked to descriptors of categories by tags, tokens, or other data elements; for instance and without limitation, first training set may be provided in fixed-length formats, formats linking positions of data to categories such as comma-separated value (CSV) formats and/or self-describing formats such as extensible markup language (XML), enabling process or devices to detect categories of data.

Still referring to FIG. 6, selection module 628 may be designed and configured to create at least a machine-learning model relating inputs representing attributes to a loss function output as described above; for instance, machine-learning model may present a linear or other mathematical combination of attribute values with weights or other expressions indicating relative importance within the linear or other mathematical combination. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure. Machine-learning may include other regression algorithms, including without limitation polynomial regression.

Continuing to refer to FIG. 6, machine-learning algorithm used to generate machine-learning model may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 6, selection module 628 may generate loss function using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 636 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms used by selection module 628 may include supervised machine-learning algorithms, which may, as a non-limiting example be executed using a supervised learning module 640 executing on selection module 628 and/or on another computing device in communication with the selection module 628, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use attributes as inputs, a loss function output as an output, and a scoring function representing a desired form of relationship to be detected between elements of a restricted nutrimental datum and information in a database of nutrimental reference set; scoring function may, for instance, seek to minimize the degree of error between generated loss function and results presented in training data 636. In an embodiment, generating at least a first filter set 120 may further include generating a loss function of user specific variables and minimizing the loss function. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 636. Persons skilled in the art, upon reviewing the entirety of this disclosure, will be aware of various possible variations of supervised machine learning algorithms that may be used to generate a mathematical function or model 644 relating attributes to loss-function outputs.

Still referring to FIG. 6, selection module 628 may alternatively or additionally be designed and configured to generate at least a selection output by executing a lazy learning process as a function of the training data 636 and the at least an adapted nutrimental request 124; lazy learning processes may be performed by a lazy learning module 648 executing on selection module 628 and/or on another computing device in communication with selection module 628, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a restricted nutrimental datum associated with an element with a database of nutrimental reference set, using training data 636. As a non-limiting example, an initial heuristic may include a ranking of at least a restricted nutrimental datum according to relation to a test type of at least an element in biological extraction database 608, one or more categories of sample type data identified in at least an element in biological extraction database 608, and/or one or more test results detected in at least an element in biological extraction database 608; ranking may include, without limitation, ranking according to significance scores of associations between elements of at least a restricted nutrimental datum and biological extraction database 608, for instance as calculated as described above. Heuristic may include selecting some number of highest-ranking associations and/or match to an element in biological extraction database 608. Selection module 628 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs relating to generation of at least a first filter set as described in this disclosure, including without limitation lazy learning applications of machine-learning algorithms as described in further detail herein.

In an embodiment, and continuing to refer to FIG. 6, selection module 628 may perform more than one loss function and/or lazy learning process; for instance, while a first loss function and/or lazy learning process may relate all attributes to a selection output 632, a second loss function and/or lazy learning process may select a most efficient physical transfer route, which in turn may be used to score route efficiencies and be input to a more global loss function, for instance by presenting to the more global loss function a list of nutrimental transfer descriptors with optimal routes. Alternatively or additionally, a current user may specify one or more attributes according to which that user wishes a selection function to be performed, eliminating use of other attributes to derive and/or perform selection function. A selection output 632 may be generated by any of the above-described processes, models, and/or modules, or any combination thereof. Persons skilled in the art, upon reviewing the entirety of this disclosure, will be aware of various ways in which selection functions may be generated and/or customized to produce selection output 632 as described in this disclosure.

In an embodiment, and referring again to FIG. 6, selection module 628 is designed and configured to select the nutrimental transfer descriptor based on the selection output 632.

Selection may include selection of a nutrimental transfer descriptor having a highest-ranked selection output 632, such as a nutrimental transfer descriptor having the lowest loss function output. Selection may include presentation of two or more nutrimental transfer descriptors to a user via user-client device 104, for instance as described above, and receiving a user selection of one of the two or more nutrimental transfer descriptors; two or more nutrimental transfer descriptors may be ranked according to one or more selection output 632 as described above. Display of nutrimental transfer descriptors may include display of all generated nutrimental transfer descriptors; alternatively or additionally a smaller subset of the generated nutrimental transfer descriptors may be displayed. A smaller subset may be selected according to any process for selecting a smaller subset as described herein, including without limitation selection of a number of nutrimental transfer descriptions associated with highest-ranked or most optimal selection output 632; for instance, where selection function is or includes a loss function, selection may include selection of a set of nutrimental transfer descriptors having the smallest loss function outputs. A number of nutrimental transfer descriptors having minimal loss function outputs and/or highest ranking selection output 632 may be set according to a number stored in memory of at least a server 112; the number may be set by a user, who may be permitted to request selection of any number of nutrimental transfer descriptors to be displayed. Alternatively or additionally, the number may be set by default; a user entry may modify number from default to another value.

Figure 7:
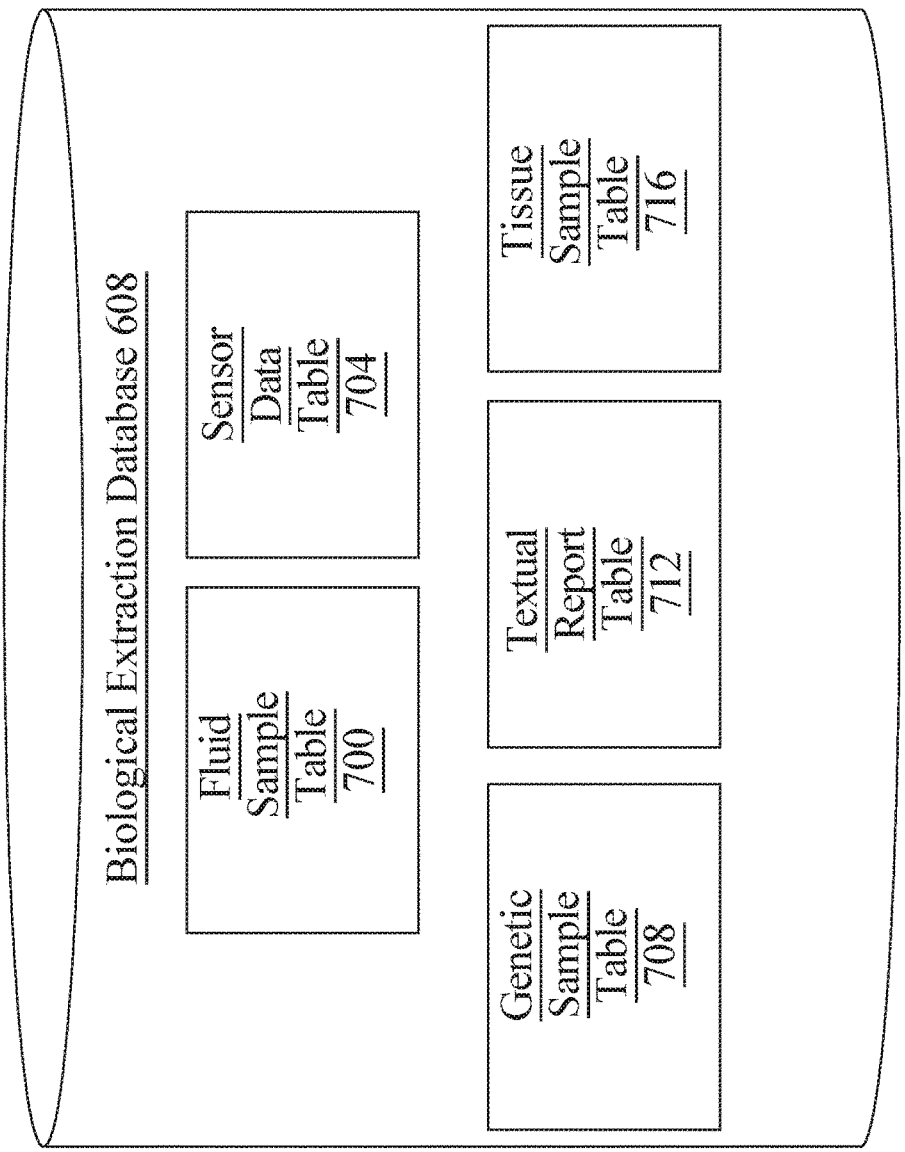
FIG. 7 is a block diagram illustrating an exemplary embodiment of a biological extraction database.

Referring now to FIG. 7, an exemplary embodiment of biological extraction database 608 is illustrated. Biological extraction database may be implemented as any database and/or datastore suitable for use as a database as described above. Biological extraction database 608 may include one or more entries listing tables associated with one or more biological extraction inputs as described above. Biological extraction database 608 may include tables listing one or more samples and/or biological extractions according to sample source. For instance, and without limitation, biological extraction database 608 may include a fluid sample table 700 listing samples that may be acquired from a person by extraction of fluids, such as without limitation blood, lymph, urine, cerebrospinal fluid, or the like for medical or diagnostic testing, as described in more detail above. Fluid sample table 700 may further contain a plurality of tests able to be performed on such fluids, along with normal and abnormal ranges for test results correlated with dietary/nutritional information of specific foods, food groups, food items, and the like. As a non-limiting example, an elevated total cholesterol and a decreased vitamin C level of a blood sample may indicate the need for a restriction filter to limit nutrimental artifacts low in fat content and high in vitamin C. As another non-limiting example, biological extraction database 608 may include a sensor data table 704, which may list samples acquired using one or more sensors, for instance as described in further detail above. Sensor data table 704 may further contain a plurality of tests able to be performed with such sensors, along with normal and abnormal ranges for test results correlated with dietary/nutritional information of specific foods, food groups, food items, and the like. As a non-limiting example, test results from a wearable device measuring blood pressure which indicates high blood pressure may indicate the need for a restriction filter to exclude nutrimental artifacts which are high in sodium and total fat. As a further non-limiting example, biological extraction database 608 may include a genetic sample table 708 which may list partial or entire sequences of genetic material, genetic diseases, genetic predispositions, and the like. Genetic material may be extracted and amplified, as a non-limiting example, using polymerase chain reactions (PCR) or the like. Genetic sample table 708 may further contain a plurality of genetic tests along with normal and abnormal results correlated with dietary/nutritional information of specific foods, food groups, food items, and the like. As a non-limiting example, results from a genetic blood test in a biological extraction input demonstrating celiac disease may indicate the need for a restriction filter to exclude nutrimental artifacts which contain gluten. As a further example, also non-limiting, biological extraction database 608 may include a textual report table 712, which may list textual descriptions of medical tests, including without limitation radiological tests, tests of strength and/or dexterity, blood tests, urine tests, sensor data or the like. This table may differentiate from other tables listed herein by textual descriptions, for example, a medical report of a complete blood count with an abnormally low platelet count reported as 90,000 platelets per mcL and a blood test indicating an abnormally low vitamin B-12 level as 100 ng per mL may indicate the need for a restriction filter via fluid sample table 700 to include foods only with high vitamin B12 levels to attempt restoration of these deficiencies, while a medical report of a complete blood count with an abnormally low platelet count reported as "low" and a blood test indicating an abnormally low vitamin B-12 level as "low" may indicate the need for a restriction filter via textual report table 712 to include foods only with high vitamin B12 levels to attempt restoration of these deficiencies. Data in textual report table 712 may be sorted and/or categorized using a language processing module, for instance, translating a textual description into a numerical value or a label corresponding to a restriction, using any known language processing algorithm or algorithms. As another non-limiting example, biological extraction database 608 may include a tissue sample table 716, which may record biological extractions obtained using tissue samples, along with normal and abnormal test results correlated with dietary/nutritional information of specific foods, food groups, food items, and the like. Tables presented above are presented for exemplary purposes only; persons skilled in the art will be aware of various ways in which data may be organized in biological extraction database 608 consistently with this disclosure. As a non-limiting example, information contained within biological extraction database 608 may be used in generating at least a first filter set as a function of at least a restricted nutrimental datum from a user-client device using mathematical algorithms, loss functions, and/or machine learning processes as described above. As another non-limiting example, information contained within biological extraction database 608 may be used in selecting at least a sustenance provider and selecting at least a physical performer using mathematical algorithms, loss functions, and/or machine learning processes as described above.

Figure 8:
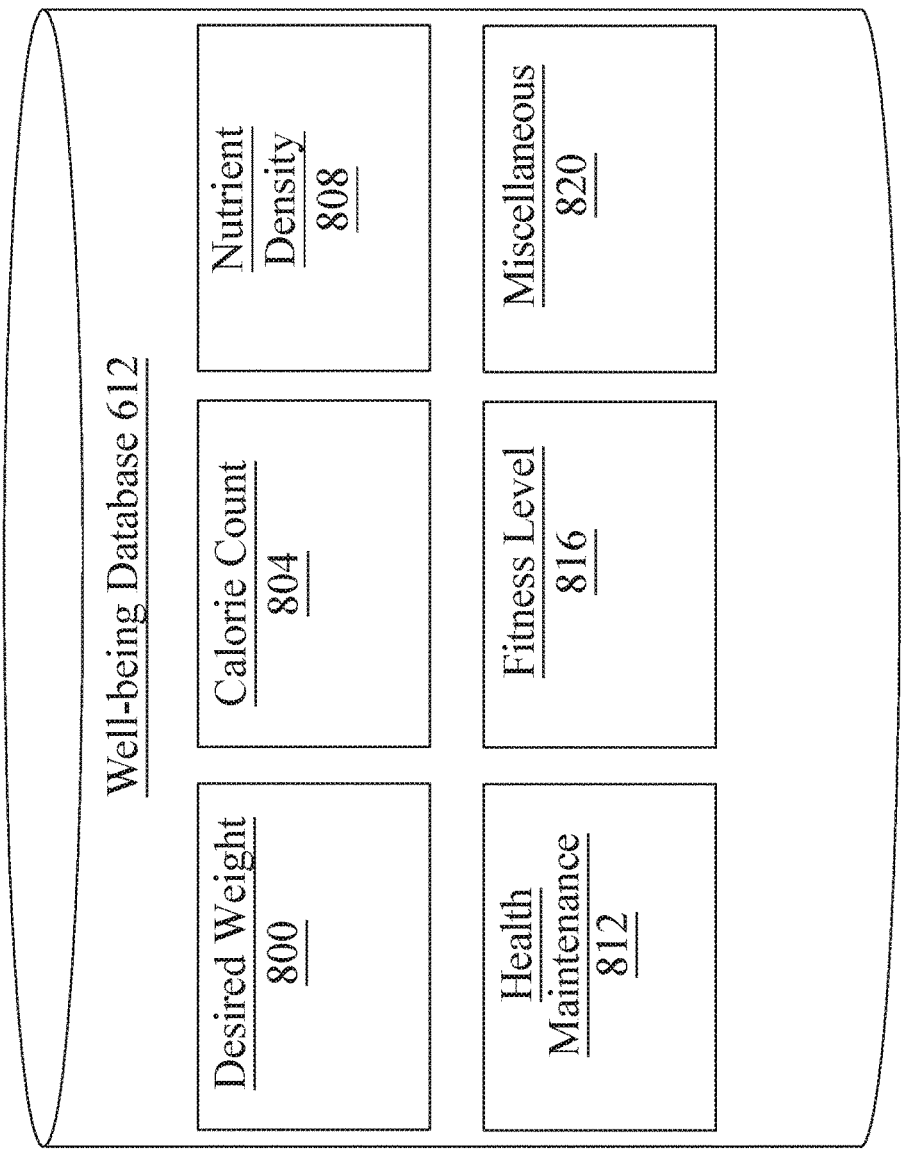
FIG. 8 is a block diagram illustrating an exemplary embodiment of a well-being input database.

Referring now to FIG. 8, an exemplary embodiment of well-being database 612 is illustrated. Well-being database may be implemented as any database and/or datastore suitable for use as a database as described above. The well-being database may include one or more entries listing tables associated with one or more well-being inputs as described above. Well-being database 612 may contain information pertaining to a user's goals within a nutrimental restriction requirement, non-limiting examples of some goals being weight-loss, weight-gain, muscle-gain, increased amount of sleep, increased stamina, increased alertness, and the like.

One or more database tables in well-being database 612 may include a desired weight table 800; desired weight table may include information describing nutritional and nutrimental information pertaining to programs for weight loss and weight gain such as what specific foods and/or items may help in achieving such goals. One or more database tables in well-being database 612 may include calorie count table 804; calorie count may include information describing the number of calories in nutrimental artifacts which may, for example, help in determining foods that will meet a user's goal of weight loss (low calorie foods). One or more database tables in well-being database 612 may include nutrient density table 808; nutrient density may include information describing all nutritional information for nutrimental artifacts presented to the user, such as total fat, calorie content, protein content, calcium, Vitamin A, Vitamin D, iron, folate, chromium, and the like; obtaining such information from robust sources such as, for example, the World Health Organization (WHO) Nutrition Landscape Information System which brings together all existing WHO Global Nutrition Databases dynamically, as well as other existing food and nutrition-related data from partner agencies. This may allow, for example, for a user to view nutritional content of all unrestricted nutrimental objects and then restrict such objects for display of restricted nutrimental objects which are low in total fat and high in fiber to meet a nutritional goal. One or more database tables in well-being database 612 may include health maintenance table 812, health maintenance may include information describing ideal nutrimental artifacts for persons of a specific sex and age. One or more database tables in well-being database 612 may include fitness level table 816, which may include information describing ideal nutrimental artifacts based on a fitness level or fitness plan of a user, such as signifying high calorie and high protein foods for a professional bodybuilder, low calorie nutrient dense foods for someone trying to stay below a certain weight to meet a sporting even weight class, high calorie nutrient dense foods for a professional runner leading up to a marathon, and the like. One or more database tables in well-being database 612 may include miscellaneous table 820, which may contain any other information not mentioned herein relating to well-being input restriction requirements of a user. Tables presented above are presented for exemplary purposes only; persons skilled in the art will be aware of various ways in which data may be organized in well-being database 612 consistently with this disclosure. As a non-limiting example, information contained within well-being database 612 may be used in generating at least a first filter set as a function of at least a restricted nutrimental datum from a user-client device using mathematical algorithms, loss functions, and/or machine learning processes as described above. As another non-limiting example, information contained within well-being database 612 may be used in selecting at least a sustenance provider and selecting at least a physical performer using mathematical algorithms, loss functions, and/or machine learning processes as described above.

Figure 9:
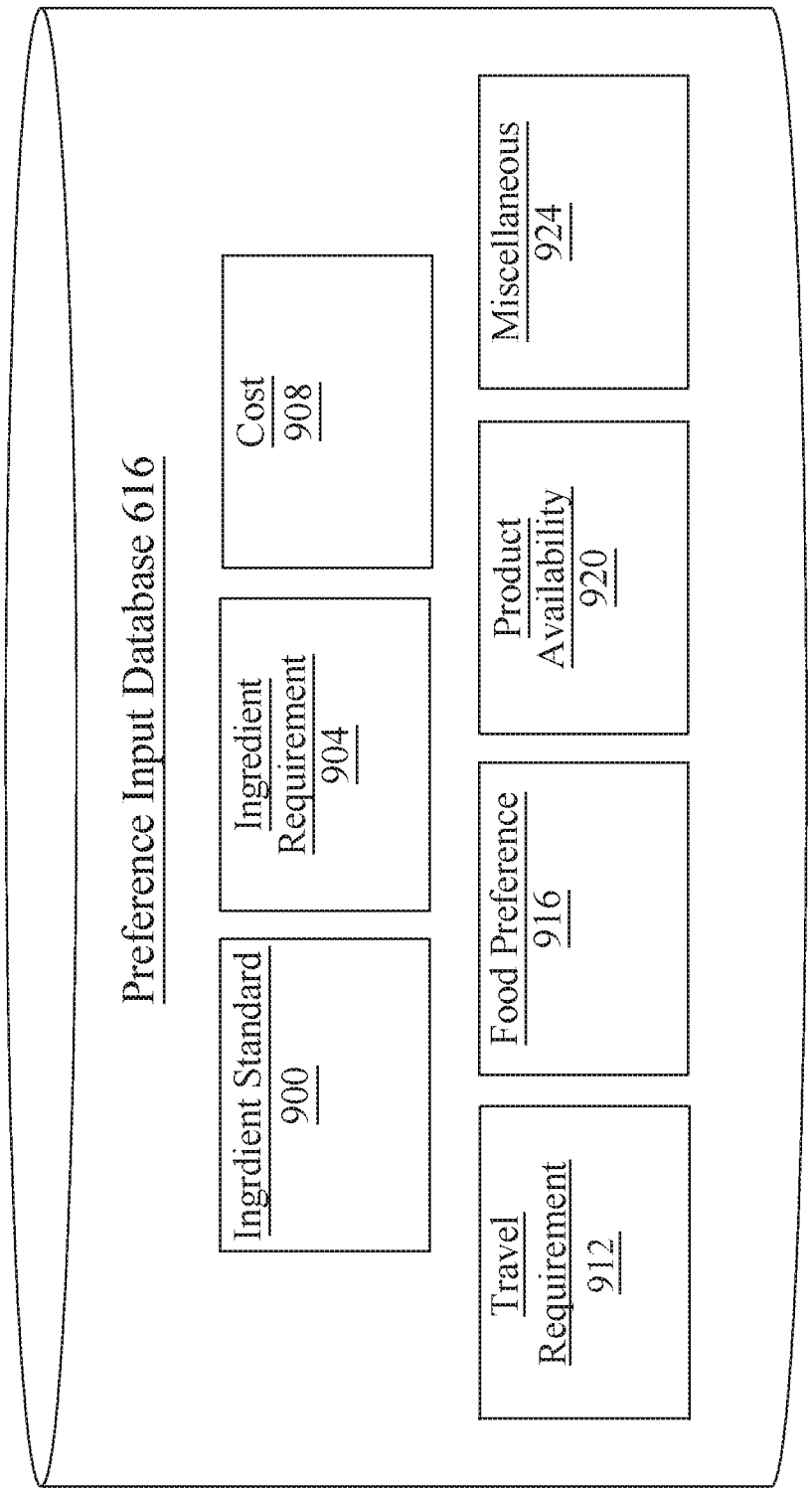
FIG. 9 is a block diagram illustrating an exemplary embodiment of a preference input database.

Referring now to FIG. 9, an exemplary embodiment of preference input database 616 is illustrated. Preference input database 616 may be implemented as any database and/or datastore suitable for use as a database as described above. Preference input database 616 may include one or more entries listing tables associated with one or more preference inputs as described above. One or more database tables in preference input database 616 may include, without limitation, an ingredient standard table 900; ingredient standard table 900 may contain information relating to quality of food such as a requirement for organic produce, wild raised seafood, sustainably grown meats, free range poultry, locally sourced products and/or ingredients, products grown without the use of pesticides and the like. One or more database tables in preference input database 616 may include without limitation, an ingredient requirement table 904; ingredient requirement table 904 may include information pertaining to certain foods or items required by a user. For example, user requesting a chicken and kale dish be cooked in grapeseed oil. One or more database tables in preference input database 616 may include without limitation, cost table 908; cost may include information relating to user cost requirement; cost requirement may include user weekly meal budget, individual meal budget, budget for specific individual items within an adapted nutrimental request, budget for specific groups of items within an adapted nutrimental request, budget for items containing certain nutritional content, and the like. One or more database tables in preference input database 616 may include without limitation, travel requirement table 912; travel requirement may include information relating to how much time a user desires their food to be in transit by a physical performer once completely prepared by a sustenance provider, specific instruction by a user for how nutrimental artifacts should be handled while in transit, and the like. One or more database tables in preference input database 616 may include without limitation, food preference table 916; food preferences may include a user's preference to consume certain foods or food groups, such as for example a user's preference to consume chicken and beef but a dislike of plant proteins such as tofu and lentils. One or more database tables in preference input database 616 may include without limitation, product availability table 920; product availability may include user request to include certain foods or ingredients that could be in addition to a main set of nutrimental artifacts order, for example a user requests five chicken dinners for the week and includes a request for chocolate cake for three of those days if the selected sustenance provider has the capacity to prepare it. One or more database tables in preference input database 616 may include without limitation, miscellaneous table 924; miscellaneous may include other user preferences that may be requested by a user but that have not been discussed above. Tables presented above are presented for exemplary purposes only; persons skilled in the art will be aware of various ways in which data may be organized in preference input database 616 consistently with this disclosure. As a non-limiting example, information contained within preference input database 616 may be used in generating at least a first filter set as a function of at least a restricted nutrimental datum from a user-client device using mathematical algorithms, loss functions, and/or machine learning processes as described above. As another non-limiting example, information contained within preference input database 616 may be used in selecting at least a sustenance provider and selecting at least a physical performer using mathematical algorithms, loss functions, and/or machine learning processes as described above.

Figure 10:
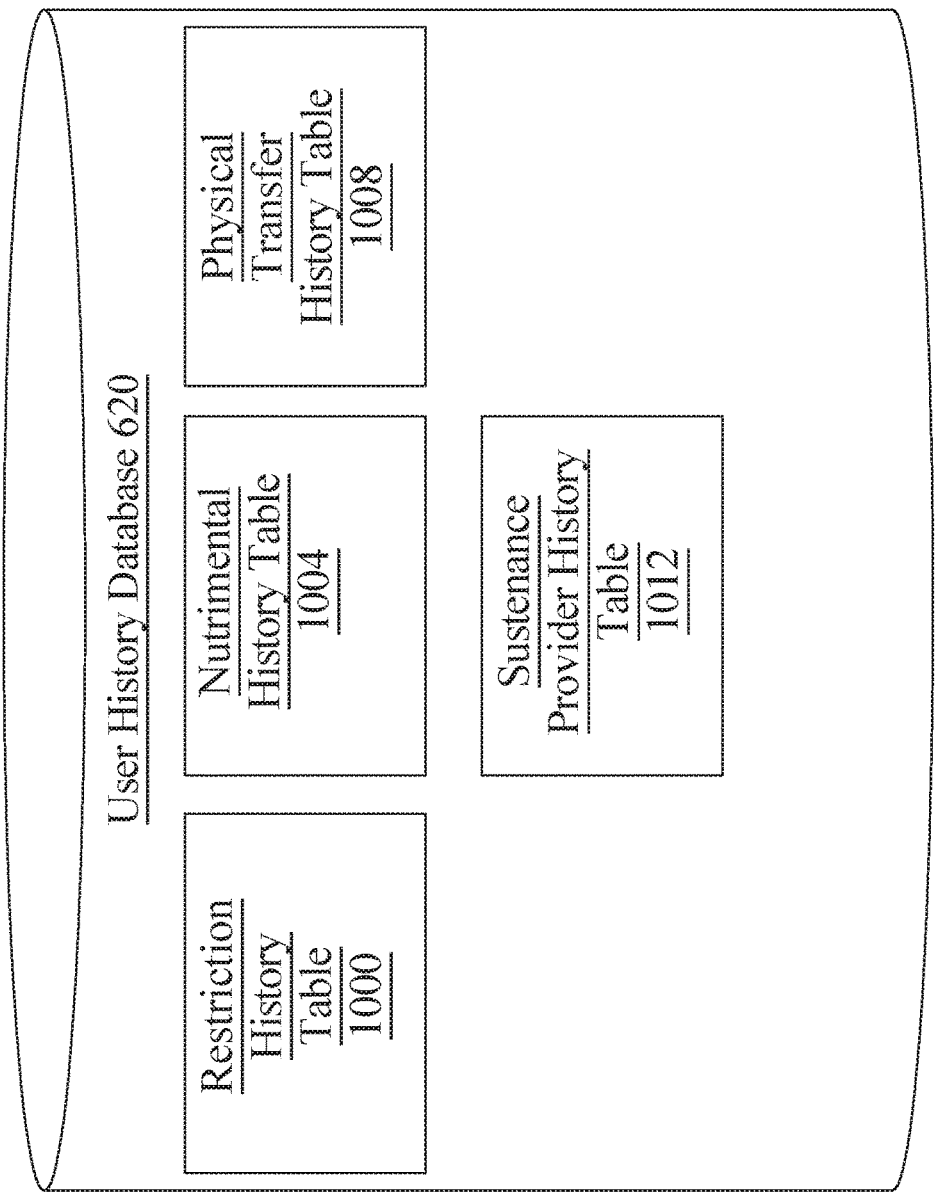
FIG. 10 is a block diagram illustrating an exemplary embodiment of a user history database.

Referring now to FIG. 10, an exemplary embodiment of a user history database 620 is illustrated. History of previous user interactions with system 100 or 600 may be stored in and/or retrieved from a user history database 620. User history database 620 may include any database, data store, and/or data structure suitable for use as collection element database as described above. User history database 620 may include one or more entries listing tables. One or more tables in user history database 620 may include a constraint history table 1000, which may list past restriction requirements of adapted nutrimental requests as described in further detail above. User history database 620 may include a nutrimental history table 1004, which may list nutrimental artifacts previously selected by user according to methods and/or systems as described herein. User history database 620 may include a physical transfer history table 1008, which may list one or more physical transfers, as described in further detail above, previously selected. User history database 620 may include a sustenance provider history table 1012, which may list one or more sustenance providers, as described in further detail above, previously selected. Tables presented above are presented for exemplary purposes only; persons skilled in the art will be aware of various ways in which data may be organized in user history database 620 consistently with this disclosure. As a non-limiting example, information contained within user history database 620 may be used in generating at least a first filter set as a function of at least a restricted nutrimental datum from a user-client device using mathematical algorithms, loss functions, and/or machine learning processes as described above. As another non-limiting example, information contained within user history database 620 may be used in selecting at least a sustenance provider and selecting at least a physical performer using mathematical algorithms, loss functions, and/or machine learning processes as described above.

Figure 11:
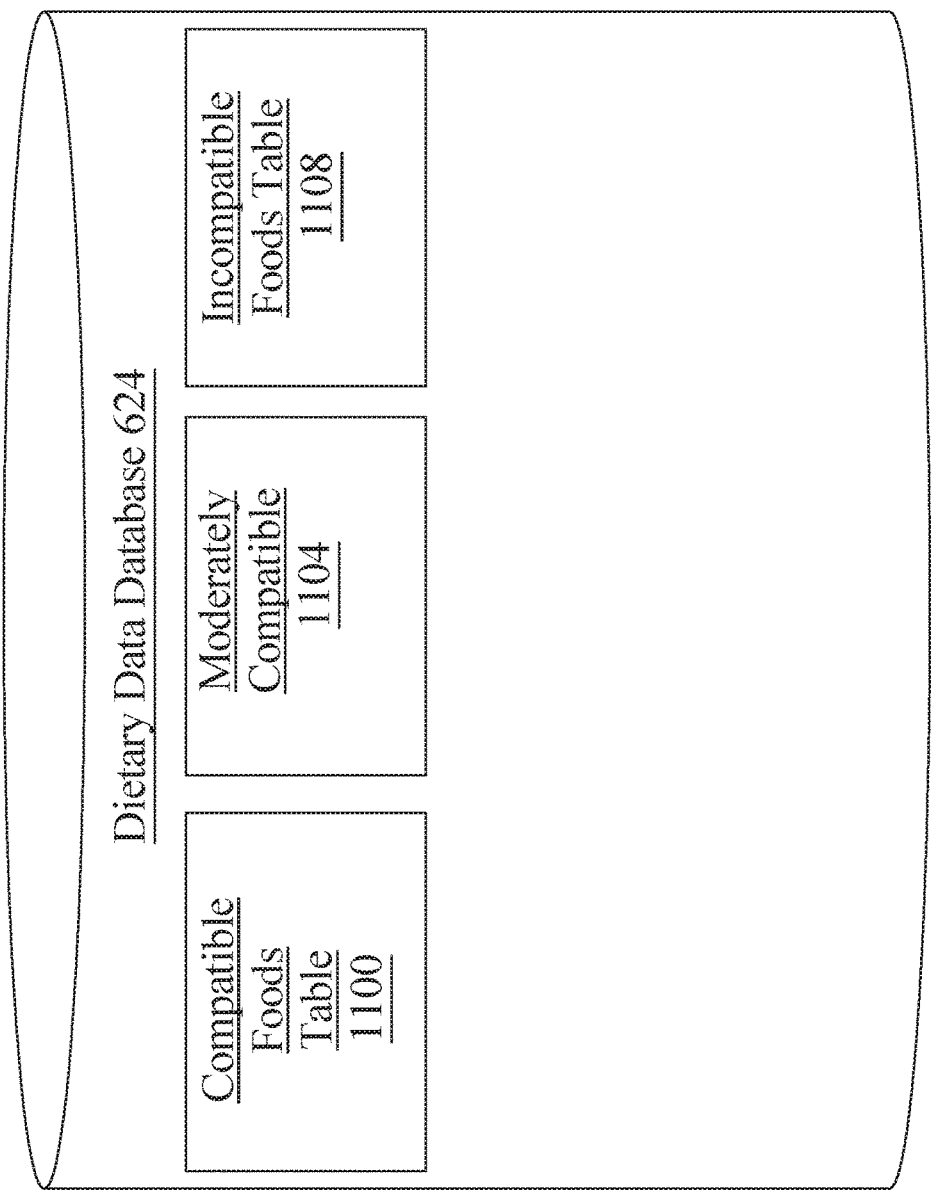
FIG. 11 is a block diagram illustrating an exemplary embodiment of a dietary data database.

Referring now to FIG. 11, an exemplary embodiment of a dietary data database 624 is illustrated. Dietary data database 624 may include any database, data store, and/or data structure suitable for use as collection element database as described above. Dietary data database 624 may include one or more entries listing tables. One or more tables in dietary data database 624 may include a compatible foods table 1100. For instance and without limitation, compatible foods table 1100 may be a table relating restriction requirements to foods that are compatible with a particular restriction requirement as described in further detail above; for instance where a restriction requirement contains a request for a ketogenic diet foods such as beef tips, ground sirloin and lamb shanks may be compatible with such a request while such foods may not be compatible with a categorical constraint for a vegan diet. Dietary data database 624 may include moderately compatible food table 1104 which may be a table relating restriction requirements to foods that are moderately compatible with a particular categorical constraint; for instance where a restriction requirement contains a request for a gluten free diet from a user with a self-reported gluten intolerance, foods such as certified gluten free oats may be moderately compatible with such a user, while certified gluten free oats may not be compatible for a user following a gluten free diet because of a previous diagnosis of Celiac Disease. For instance and without limitation, dietary data database 624 may include as a non-limiting example, incompatible food table 1108. For instance and without limitation, incompatible food table 1108 may include a table relating categorical constraints to foods that are incompatible with a particular restriction requirement; for instance where a restriction requirement contains a request for a corn free diet ingredients such as cornstarch, corn oil, dextrin, maltodextrin, dextrose, fructose, ethanol, maize, and/or sorbitol may be listed. In an embodiment, database tables contained within dietary data database 624 may include groupings of foods by different categories such as grains, meats, vegetables, fruits, sugars and fats and the like. In an embodiment, database tables contained within dietary data database 624 may include groups of foods by ingredients that a food may be comprised of, for example gravy may contain flour which may contain gluten. Tables presented above are presented for exemplary purposes only; persons skilled in the art will be aware of various ways in which data may be organized in user dietary data database 624 consistently with this disclosure. As a non-limiting example, information contained within dietary database 620 may be used in generating at least a first filter set as a function of at least a restricted nutrimental datum from a user-client device using mathematical algorithms, loss functions, and/or machine learning processes as described above. As another non-limiting example, information contained within dietary database 620 may be used in selecting at least a sustenance provider and selecting at least a physical performer using mathematical algorithms, loss functions, and/or machine learning processes.

Figure 12:
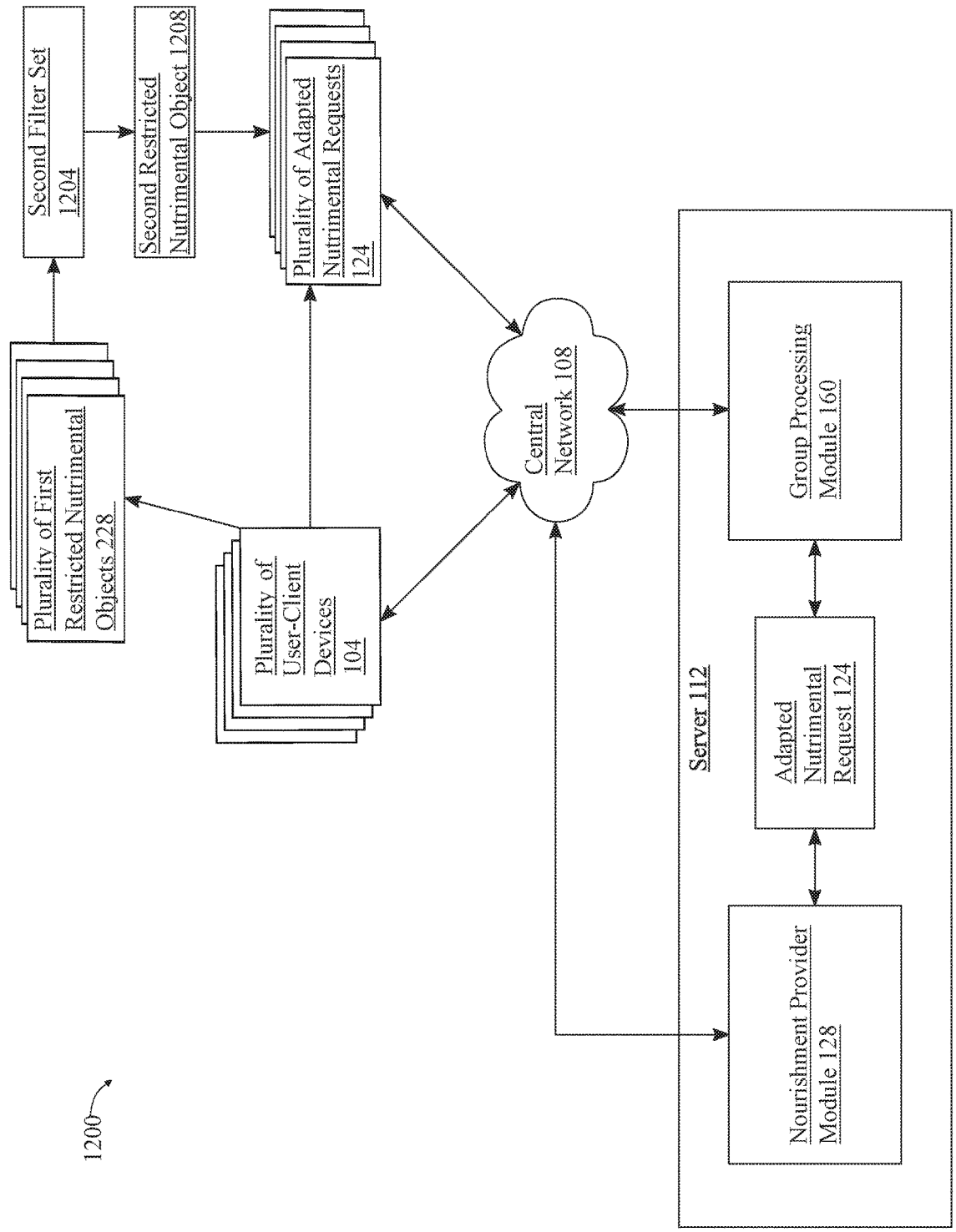
FIG. 12 is a block diagram illustrating an exemplary embodiment of a group ordering schema.

Now referring to FIG. 12, an exemplary embodiment of a group ordering schema 1200 is illustrated. Group ordering schema 1200 may include a group processing module 160 operating on the at least a server 112. Group processing module 160 may be designed and configured to receive a plurality of adapted nutrimental requests 124 from a plurality of user-client devices 104 and generate at least an adapted nutrimental request 124 containing at least a group identifier as a function of the plurality of adapted nutrimental requests 124. At least an adapted nutrimental request 124 may be transmitted in a group ordering schema via group processing module 160 if at least a group identifier accompanies the at least an adapted nutrimental request 124. At least a group identifier may indicate selection by a user on a user-client device 104 for the desire to be part of a group ordering schema which, in an embodiment, may permit a plurality of adapted nutrimental requests 124 from a plurality of user-client devices 104 to be processed as a sole at least an adapted nutrimental request 124 on the at least a server 112. In an embodiment, group ordering schema 1200 may allow adapted nutrimental artifacts that meet the needs of numerous individuals to be delivered to one location at a certain frequency, where a plurality of user-client devices 104 may transmit a plurality of adapted nutrimental requests 124 to at least a central network 108 and group processing module 160 operating on the at least a server 112 may generate at least an adapted nutrimental request 124 as a function of the plurality adapted nutrimental request 1024 transmitted. As a non-limiting example, three family members want five meals each for dinner to be delivered to their home once a week for the next three months, each having different food requirements, such as one family member requiring meals to be dairy-free, the second family member requiring meals to be grain-free and be low in sodium, and the third family member requiring meals which fall under a vegan diet. Continuing the non-limiting example, each of the three family members may each use their own user-client device 104 to join a group ordering schema and submit at least an adapted nutrimental request 124, with group identifier, that corresponds to their individual nutrimental restrictions, the plurality of adapted nutrimental requests 124 being transmitted to a central network 108 containing at least a server 112 wherein a group processing module 160 may generate a single at least an adapted nutrimental request 124 by combing the plurality of adapted nutrimental requests 124, wherein the single at least an adapted nutrimental request 124 may then be processed by nourishment provider module 128 for selection of at least a sustenance provider and at least a physical performer as described above and throughout this disclosure herein.

With continued reference to FIG. 12, generating the at least an adapted nutrimental request 124 may include generating at least a second filter set 1204 as a function of a plurality of first restricted nutrimental objects 228 and receiving a plurality of adapted nutrimental requests 124 as a function of a selection from at least a second restricted nutrimental object 1208 of the at least a second filter set 1204. Generation of the at least a second filter set 1204 for receipt by the plurality of user-client devices 104 may be generated by similar means to that of at least a first filter set 120 generation as described above in reference to FIG. 1 and FIG. 2, except where the plurality of first restricted nutrimental objects 228 may be the input for the at least a second filter set 1204 generation and an at least a restricted nutrimental datum may be the input for the at least a first filter set 120 generation. Generation of the at least a second restricted nutrimental object 1208 for display on each user-client device in the plurality of user-client devices 104 may be generated by similar means to that of at least a first restricted nutrimental object 220 generation as described above in reference to FIG. 1 and FIG. 2, except where the selection of at least a second filter set 1204 may be the input for the at least a second restricted nutrimental object 1208 generation and the selection of at least a first filter set 120 may be the input for the at least a first restricted nutrimental object 220 generation. In an embodiment, group ordering schema 1200 with such mentioned limitation herein may allow adapted nutrimental artifacts that meet the needs of all individuals in a group be delivered to one location at a certain frequency. A plurality of first restricted nutrimental objects 228 may be transmitted in a group ordering schema via group processing module 160 if at least a group identifier accompanies the plurality of first restricted nutrimental objects 228. At least a group identifier may indicate selection by a user on a user-client device 104 for the desire to be part of a group ordering schema which, in an embodiment, may permit a plurality of first restricted nutrimental objects 228 from a plurality of user-client devices 104 to be used for generation of at least a second filter set 1204. As a non-limiting example, three family members may want five meals each for dinner to be delivered to their home once a week for the next three months, each having different food requirements, such as one family member requiring meals to be dairy-free, the second family member requiring meals to be grain-free and be low in sodium, and the third family member requiring meals which fall under a vegan diet. Continuing the non-limiting example, each of the three family members may each use their own user-client device 104 to join a group ordering schema, filter out nutrimental artifacts which do not meet each individual's mentioned restrictions with at least a first filter set 120, and submit the resulting individual at least a first restricted nutrimental objects, with group identifier, as a plurality of first nutrimental objects 228 to a central network 108. Continuing the non-limiting example, group processing module 160 may generate at least a second filter set 1204 as a function of the submitted plurality of first restricted nutrimental objects 228, wherein the at least a second filter set 1204 may only allow display of nutrimental artifacts which are all dairy-free, grain-free, low in sodium, and vegan—this display being the at least a second restricted nutrimental object 1208. Other filters may be imposed by each individual to further restrict nutrimental artifacts if the four criteria mentioned are still met. Continuing the non-limiting example, each individual may submit at least an adapted nutrimental request 124 via selection from the at least a second restricted nutrimental object 1208, all three of the submitted at least an adapted nutrimental requests being transmitted to the central network 108 as a plurality of adapted nutrimental requests 124 wherein the group processing module 160 on at least a server 112 may generate a single at least an adapted nutrimental request 124 by combing the plurality of adapted nutrimental requests 124, wherein the single at least an adapted nutrimental request 124 may then be processed by nourishment provider module 128 for selection of at least a sustenance provider and at least a physical performer as described throughout this disclosure, with emphasized reference to FIG. 1 and FIG. 6.

Figure 13:
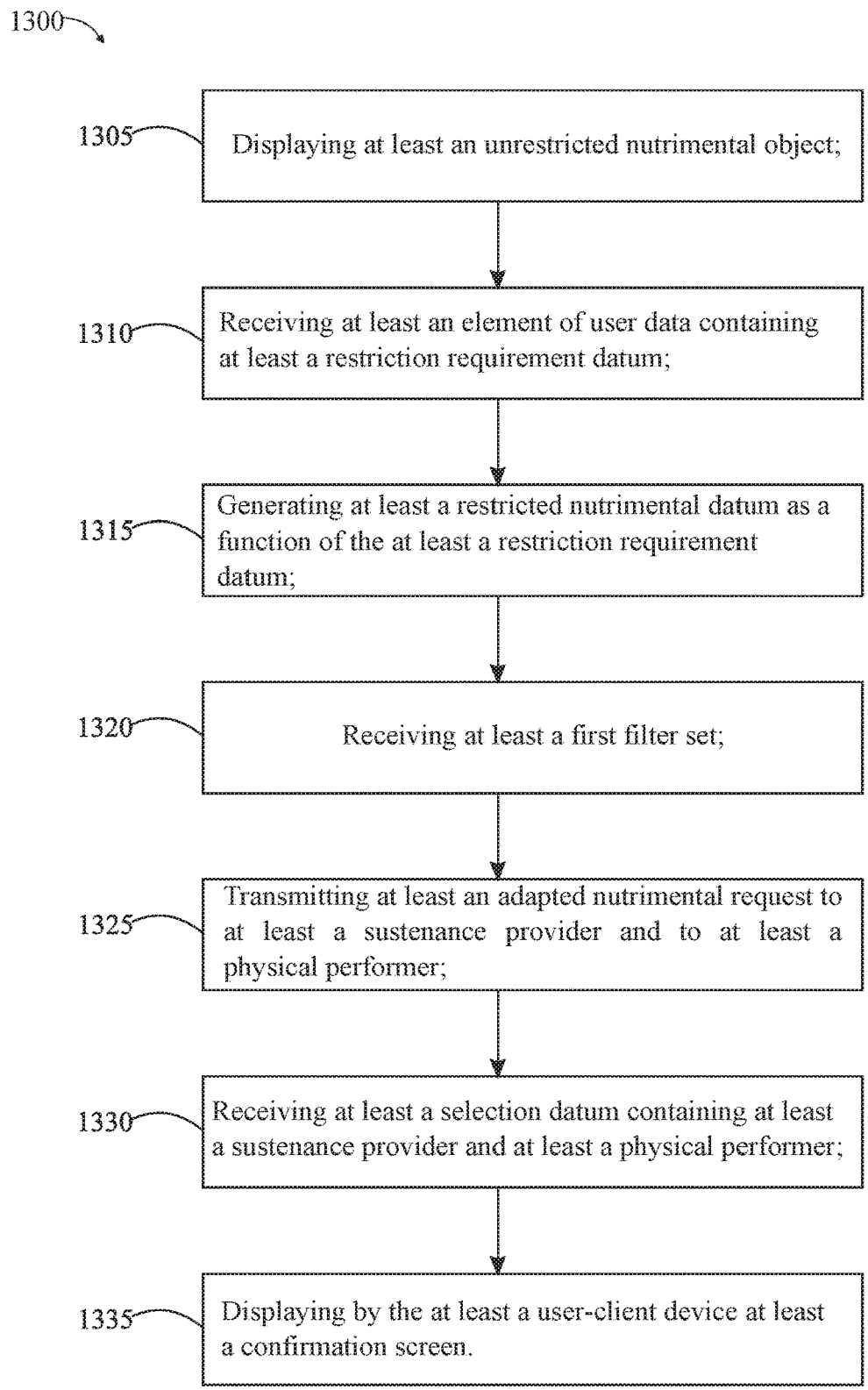
FIG. 13 is a flow diagram illustrating an exemplary embodiment of a method of generating restriction requirements with a user-client device for transport of adapted nutrimental artifacts is illustrated.

Referring now to FIG. 13, a method 1300 of generating restriction requirements with a user-client device for transport of adapted nutrimental artifacts using artificial intelligence is illustrated. At step 1305, a user-client device 104 displays at least an unrestricted nutrimental object 220. This may be implemented, for instance, as described above in reference to FIGS. 1-12. At step 1310, user-client device 104 receives at least an element of user data containing at least a restriction requirement datum 216. This may be implemented, for instance, as described above in reference to FIGS. 1-12. Receiving the at least a restriction requirement datum 216 may further include receiving at least a restriction requirement datum 216 containing at least a biological extraction input. This may be implemented, for instance, as described above in reference to FIGS. 1-12. Receiving the at least a restriction requirement datum 216 may include receiving a restriction requirement datum 216 containing at least a well-being input containing at least a well-being goal. This may be implemented, for instance, as described above in reference to FIGS. 1-12. Receiving the at least a restriction requirement datum 216 may include receiving at least a restriction requirement datum 216 containing at least a preference input containing at least a terminal location. This may be implemented, for instance, as described above in reference to FIGS. 1-12.

At step 1315, and still referring to FIG. 13, user-client device 104 generates at least a restricted nutrimental datum as a function of the at least a restriction requirement datum 216. This may be implemented, for instance, as described above in reference to FIGS. 1-12. Generating the at least a restricted nutrimental datum may include receiving at least a user input variable wherein the at least a user input variable further comprises at least a user nutrimental preference input, generating a loss function as a function of the at least a user input variable, minimizing the loss function. This may be implemented, for instance, as described above in reference to FIGS. 1-12.

At step 1320, user-client device 104 receives an at least a first filter set 120. This may be implemented, for instance, as described above in reference to FIGS. 1-12. Receiving at least a first filter set 120 may include receiving at least a body intolerability score. This may be implemented, for instance, as described above in reference to FIGS. 1-12. Receiving an at least a first filter set 120 may include receiving at least a user aversion score. This may be implemented, for instance, as described above in reference to FIGS. 1-12.

At step 1325, and still referring to FIG. 13, user-client device 104 transmits at least an adapted nutrimental request 124 to at least a sustenance provider and to at least a physical performer. This may be implemented, for instance, as described above in reference to FIGS. 1-12. Transmitting the at least an adapted nutrimental request 124 may include transmitting at least an element of user data and at least a nutrimental artifact. This may be implemented, for instance, as described above in reference to FIGS. 1-12. Transmitting the at least an adapted nutrimental request 124 may include filtering the at least an unrestricted nutrimental object 220 as a function of the at least a first filter set 120, displaying at least a first restricted nutrimental object 228 as a function of receiving a selection from the at least a first filter set 120, and generating the at least an adapted nutrimental request 124 as a function of receiving a selection from the at least a first restricted nutrimental object 228. This may be implemented, for instance, as described above in reference to FIGS. 1-12.

At step 1330, and still referring to FIG. 13, user-client device 104 receives at least a selection datum of the at least a sustenance provider and to the at least a physical performer. This may be implemented, for instance, as described above in reference to FIGS. 1-12. Receiving the at least a selection datum containing the at least a sustenance provider and the at least a physical performer may include joining a plurality of user-client devices 104 in a group ordering schema, receiving a group identifier of the group ordering schema, and transmitting at least an adapted nutrimental request 124 of a plurality of adapted nutrimental requests 124. This may be implemented, for instance, as described above in reference to FIGS. 1-12. Transmitting the at least an adapted nutrimental request 124 of the plurality of nutrimental requests 124 may include transmitting at least a first restricted nutrimental object 228 of a plurality of first restricted nutrimental objects 228, receiving at least a second filter set 1204 as a function of the plurality of first restricted nutrimental objects 228, displaying at least a second restricted nutrimental object 1208 as a function of a selection from the at least a second filter set 1204, and generating at least an adapted nutrimental request 124 as a function of a selection from the at least a second restricted nutrimental object 1208. This may be implemented, for instance, as described above in reference to FIGS. 1-12. At step 1335, user-client device 104 displays at least a confirmation screen. This may be implemented, for instance, as described above in reference to FIGS. 1-12.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
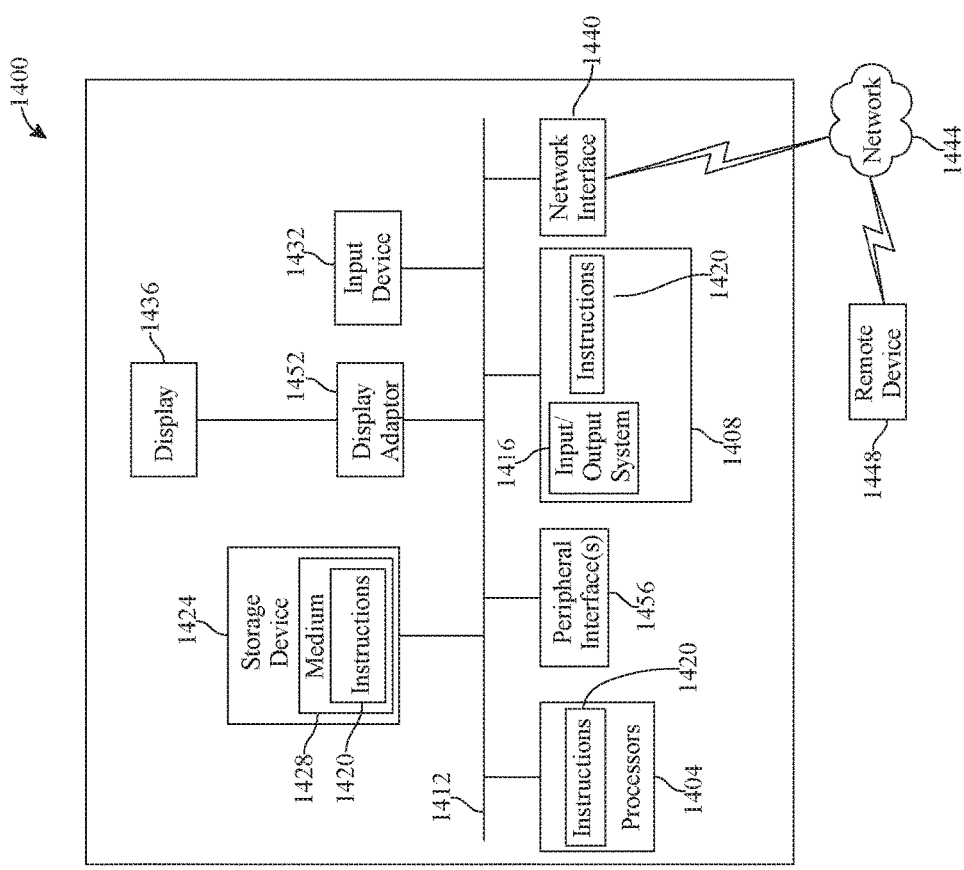
FIG. 14 is a block diagram of a computing system that can be used to implement any one or more of the methodologies disclosed herein and any one or more portions thereof.

Referring now to FIG. 14, which shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Memory 1408 may include various components (e.g., machine-readable media) including, but not limited to, a random access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for arranging transport of adapted nutrimental artifacts with user-defined restriction requirements using artificial intelligence, the system comprising:
   at least a user-client device associated with a user and containing at least an exhibition element and a processor and connected to at least a central network, the at least a user-client device designed and configured to:
     display at least an unrestricted nutrimental object on the at least an exhibition element;
     generate a restricted nutrimental datum, wherein generating the restricted nutrimental datum comprises recording an allergy test of the user;
     transmit the at least a restricted nutrimental datum;
     generate a restricted nutrimental object, wherein generating the restricted nutrimental object comprises filtering the unrestricted nutrimental object according to a filter of the at least a first filter set;
     generate at least an adapted nutrimental request, wherein generating the at least an adapted nutrimental request comprises selecting a nutrimental artifact from the restricted nutrimental object;
     transmit the at least an adapted nutrimental request, said at least an adapted nutrimental request identifying the selected nutrimental artifact; and
     receive a selection of at least a sustenance provider and a selection of at least a physical performer;
   at least a server, connected to the at least a central network, the at least a server designed and configured to receive the at least a restricted nutrimental datum;
   a nutrimental processing module operating on the at least a server, the nutrimental processing module designed and configured to:
     generate, at least a first filter set by a machine learning model, the machine learning model trained by a training set comprising restricted nutrimental data, the machine learning model configured to receive the allergy test of the user as inputs and output the at least the first filter set; and transmit the at least a first filter set to the at least a user-client device;

and a nourishment provider module operating on the at least a server, the nourishment provider module designed and configured to:

receive the at least an adapted nutrimental request;

receive at least a sustenance provider datum, and at least a physical performer datum;

generate at least a sustenance provider instruction set and at least a physical performer instruction set as a function of the at least a sustenance provider datum and the at least a physical performer datum and the identified nutrimental artifact;

select the at least a sustenance provider and the at least a physical performer as a function of the at least a sustenance provider instruction set and the at least a physical performer instruction set, wherein selecting a sustenance provider further comprises:

generating a loss function wherein the loss function comprises a machine-learning model trained by a training set comprising using nutrimental preferences, wherein the machine learning model is configured to receive at least a user nutrimental preference as inputs and output the loss function; and minimizing the loss function; and transmit the selection of the at least a sustenance provider and the selection of the at least a physical performer to the at least a user-client device.

2. The system of claim 1, wherein transmitting the at least a restricted nutrimental datum by the at least a user-client device further comprises:

displaying by the at least a user-client device, a discretionary restriction requirement field; and uploading at least a restriction requirement datum to the discretionary restriction requirement field.

3. The system of claim 1, wherein transmitting the at least an adapted nutrimental request from the at least a user-client device further comprises transmitting at least an element of user data and at least a nutrimental artifact.

4. The system of claim 1, wherein selecting the at least a sustenance provider and the at least a physical performer further comprises:

producing a field of combinations of the at least a sustenance provider and the at least a physical performer; and selecting the at least a sustenance provider and the at least a physical performer using a lazy-learning process.

5. The system of claim 1, wherein selecting the at least a sustenance provider and selecting the at least a physical performer further comprises transmitting a subset of data associated with at least a user to the at least a sustenance provider and to the at least a physical performer.

6. The system of claim 1, wherein the at least a server further comprises: a group processing module operating on the at least a server, the group processing module designed and configured to:

receive a plurality of adapted nutrimental requests from a plurality of user-client devices; and generate at least an adapted nutrimental request containing at least a group identifier as a function of the plurality of adapted nutrimental requests.

7. The system of claim 6, wherein generating the at least an adapted nutrimental request further comprises:

generating at least a second filter set as a function of a plurality of first restricted nutrimental objects; and receiving a plurality of adapted nutrimental requests as a function of receiving a selection from at least a second restricted nutrimental object of the at least a second filter set.

8. A method of generating restriction requirements with at least a user-client device for transport of adapted nutrimental artifacts using artificial intelligence, the method comprising:

displaying, by at least a user-client device, at least an unrestricted nutrimental object;

generating, by the at least a user-client device, a restricted nutrimental datum, wherein generating the restricted nutrimental datum comprises recording an allergy test of the user, and wherein generating the restricted nutrimental datum further comprises:

receiving at least a user input variable wherein the at least a user input variable further comprises at least a user nutrimental preference input;

generating a loss function wherein the loss function comprises a machine-learning model trained by a training set comprising user nutrimental preferences, wherein the machine learning model is configured to receive at least a user nutrimental preferences as inputs and output the loss function; and minimizing the loss function;

receiving, by the at least a user-client device, at least a first filter set, said first filter set generated by a machine learning model trained by a training set comprising at least restricted nutrimental data, the machine learning model configured to receive the allergy test as inputs and output a first filter set;

generating, by the at least a user-client device, a restricted nutrimental object, wherein generating the restricted nutrimental object comprises filtering the unrestricted nutrimental object according to at least a first filter set;

generating, by the at least a user-client device, at least an adapted nutrimental request, wherein generating the at least an adapted nutrimental request comprises selecting a nutrimental artifact from the restrict nutrimental object;

transmitting by the at least a user-client device at least an adapted nutrimental request to at least a sustenance provider and to at least a physical performer, said at least an adapted nutrimental request identifying the selected nutrimental artifact;

receiving by the at least a user-client device at least a selection datum containing at least a sustenance provider and at least a physical performer; and displaying by the at least a user-client device at least a confirmation screen.

9. The method of claim 8, wherein receiving the at least a restriction requirement datum further comprises receiving at least a restriction requirement datum generated as a function of at least a biological extraction input.

10. The method of claim 8, wherein receiving the at least a restriction requirement datum further comprises receiving at least a restriction requirement datum containing at least a nutrition plan and data indicating a user's desire to gain muscle mass.

11. The method of claim 8, wherein receiving at least a restriction requirement datum further comprises receiving at least a restriction requirement datum containing at least a preference input including at least a terminal location.

12. The method of claim 8, wherein receiving the at least a first filter set further comprises receiving at least a body intolerability score.

13. The method of claim 8, wherein receiving the at least a first filter set further comprises receiving at least a user aversion score.

14. The method of claim 8, wherein transmitting the at least an adapted nutrimental request further comprises transmitting at least an element of user data and at least a nutrimental artifact.

15. The method of claim 8, wherein receiving the at least a selection datum containing the at least a sustenance provider and the at least a physical performer further comprises:

joining a plurality of user-client devices in a group ordering schema;

receiving a group identifier of the group ordering schema; and transmitting at least an adapted nutrimental request of a plurality of adapted nutrimental requests.

16. The method of claim 15, wherein transmitting the at least an adapted nutrimental request of the plurality of nutrimental requests further comprises:

transmitting at least a first restricted nutrimental object of a plurality of first restricted nutrimental objects;

receiving at least a second filter set as a function of the plurality of first restricted nutrimental objects;

displaying at least a second restricted nutrimental object as a function of a selection from the at least a second filter set; and generating at least an adapted nutrimental request as a function of the selection from the at least a second restricted nutrimental object.

* * * * *